US007361343B2

(12) United States Patent
Young et al.

(10) Patent No.: US 7,361,343 B2
(45) Date of Patent: Apr. 22, 2008

(54) CYTOTOXICITY MEDIATION OF CELLS EVIDENCING SURFACE EXPRESSION OF CD63

(75) Inventors: David S. F. Young, Toronto (CA); Susan E. Hahn, Toronto (CA); Helen P. Findlay, Toronto (CA); Luis A. G. da Cruz, Toronto (CA)

(73) Assignee: Arius Research Inc., Toronto, Ontario (CA)

( * ) Notice: Subject to any disclaimer, the term of this patent is extended or adjusted under 35 U.S.C. 154(b) by 384 days.

(21) Appl. No.: 10/810,751

(22) Filed: Mar. 26, 2004

(65) Prior Publication Data

US 2004/0258693 A1    Dec. 23, 2004

Related U.S. Application Data

(63) Continuation-in-part of application No. 10/603,006, filed on Jun. 23, 2003, which is a continuation-in-part of application No. 10/348,231, filed on Jan. 21, 2003, now Pat. No. 7,009,040.

(51) Int. Cl.
*A61K 39/395* (2006.01)
*A61K 39/00* (2006.01)
*C07K 16/00* (2006.01)
*C12P 21/08* (2006.01)

(52) U.S. Cl. .................. 424/141.1; 424/155.1; 424/181.1; 424/183.1; 424/133.1; 530/388.1; 530/391.1; 530/391.7

(58) Field of Classification Search .............. 424/130.1
See application file for complete search history.

(56) References Cited

U.S. PATENT DOCUMENTS

| 4,861,581 | A | 8/1989 | Epstein et al. |
|---|---|---|---|
| 5,171,665 | A | 12/1992 | Hellstrom et al. |
| 5,296,348 | A | 3/1994 | Rakowicz-Szulczynska et al. |
| 5,484,596 | A | 1/1996 | Hanna, Jr. et al. |
| 5,693,763 | A | 12/1997 | Codington et al. |
| 5,750,102 | A | 5/1998 | Eisenbach et al. |
| 5,780,033 | A | 7/1998 | Torchilin et al. |
| 5,783,186 | A | 7/1998 | Arakawa et al. |
| 5,849,876 | A | 12/1998 | Linsley et al. |
| 5,869,045 | A | 2/1999 | Hellstrom et al. |
| 5,869,268 | A | 2/1999 | Kudo et al. |
| 6,180,357 | B1 | 1/2001 | Young et al. |
| 7,009,040 | B2 * | 3/2006 | Young et al. ............ 530/388.1 |
| 2003/0211498 | A1 | 11/2003 | Morin et al. |
| 2004/0105816 | A1 | 6/2004 | Young et al. |
| 2004/0141913 | A1 | 7/2004 | Young et al. |
| 2004/0141915 | A1 | 7/2004 | Young et al. |
| 2004/0180002 | A1* | 9/2004 | Young et al. .............. 424/1.49 |
| 2004/0197328 | A1 | 10/2004 | Young et al. |

FOREIGN PATENT DOCUMENTS

| CN | 1326951 A | 12/2001 |
|---|---|---|
| CN | 1326962 A | 12/2001 |
| CN | 1351054 A | 5/2002 |
| CN | 1364803 A | 8/2002 |
| WO | WO01/075177 | 10/2001 |
| WO | WO02/55551 | 7/2002 |
| WO | WO03/086456 | 10/2003 |

OTHER PUBLICATIONS

Taber's Cyclopedic Medical Dictionary (1985, F.A. Davis Company, Philadelphia, p. 274).*
Buskens, C et al, (Digestive Disease Week Abstracts and Itinerary Planner, 2003, abstract No. 850).*
Krontiris and Capizzi (Internal Medicine, 4th Edition, Editor-in-chief Jay Stein, Elsevier Science, 1994 Chapters 71-72, pp. 699-729).*
Carter, S. K. et al. Chemotherapy of Cancer; Second edition; John Wiley & Sons: New York, 1981; appendix C.*
Gura (Science, 1997, 278:1041-1042).*
(Roitt et al., Immunology, Fourth Edition (Mosby, London England) p. 1.6-1.7).*
Presta et al., (Biochemical Society Transactions, 30(4):487-490, 2002).*
Winter et al (TIPS, 1993, 14:139-143).*
Baselga et al (J. Clin. Oncol, 1996, 14:737-744).*
Kimball (Introduction to Immunology, 3rd ed. Macmillan, Inc, New York, 1990, p. 507).*
Miller and Tannock (The Basic Science of Oncology, 2nd ed., McGraw-Hill Inc., 1992, Ch.14).*
Kaiser (Science, 2006, 313, 1370).*
M. Martinez-Lorenzo et al, "Unusual intracellular trafficking of *Salmonella typhimurium* in human melanoma cells", Cellular Microbiology, 3(6):407-416 (2001).
H. Okochi et al, "Expression of tetra-spans transmembrane family (CD9, CD37, CD53, CD63, CD81 and CD82) in normal and neoplastic human keratinocytes: an association of CD9 with alpha3beta1 integrin", British Journal of Dermatology, 137:856-863 (1997).
J-M. Escola et al, "Selective enrichment of tetraspan proteins on the internal vesicles of multivesicular endosomes and on exosomes secreted by human B-lymphocytes", J. Biol. Chem., 273(32):20121-20127 (Aug. 1998).
A. Engering et al, "Association of distinct tetraspanins with MHC class II molecfules at different subcellular locations in human immature dendritic cells", International Immunology, 13(2):127-134 (2001).
P. Sincock et al, "Localization of the transmembrane 4 superfamily (TM4SF) member PETA-3 (CD151) in normal human tissues: comparison with CD9, CD63, and alpha5beta1 integrin", J. Histochem Cytochem, 45:515-525 (1997).

(Continued)

*Primary Examiner*—Susan Ungan
*Assistant Examiner*—Peter J. Reddig
(74) *Attorney, Agent, or Firm*—McHale & Slavin, P.A.

(57) ABSTRACT

This invention relates to the diagnosis and treatment of cancerous diseases, particularly to the mediation of cytotoxicity of tumor cells; and most particularly to the use of cancerous disease modifying antibodies (CDMAB), optionally in combination with one or more chemotherapeutic agents, as a means for initiating the cytotoxic response. The invention further relates to binding assays which utilize the CDMABs of the instant invention.

10 Claims, 21 Drawing Sheets

OTHER PUBLICATIONS

F. Berditchevski et al, "Characterization of integrin-tetraspanin adhesion complexes: role of tetraspanins in integrin signaling", J. Cell Biol., 146(2):477-492 (Jul. 1999).
R. Yauch et al, "Specific interactions among transmembrane 4 superfamily (TM4SF) proteins and phosphoinositide 4-kinase", Biochem. J., 351:629-637 (2000).
A. Zannettino et al, "Molecular cloning of the cell surface antigen identified by the osteoprogenitor-specific monoclonal antibody, HOP-26", J. Cell. Biochem., 89:56-66 (2003).
C. Joyner et al, "Identification and enrichment of human osteoprogenitor cells by using differentiation stage-specific monoclonal antibodies", Bone, 21(1):1-6 (Jul. 1997).
D. Azorsa et al, "A general approach to the generation of monoclonal antibodies against members of the tetraspanin superfamily using recombinant GST fusion proteins", J. Immunol. Meth., 229:35-48 (1999).
T. Martin, "Phosphoinositide lipids as signaling molecules: common themes for signal transduction, cytoskeletal regulation, and membrane trafficking", Annu. Rev. Cell Dev. Biol., 14:231-264 (1998).
J. Hildreth et al, "Characterization of a novel self-associating Mr 40,000 platelet glycoprotein", Blood, 77 (1):121-132 (Jan. 1991).
R. Stephen et al, "A novel oestrogen-regulated gene in human breast cancer cells identified by differential display", J. Mol. Endocrin., 20:375-380 (1998).
G. Andreola et al, "Induction of lymphocyte apoptosis by tumor cell secretion of FasL-bearing microvesicles", J. Exp. Med., 195(10):1303-1316 (May 2002).
H-I. Jang et al, "A decrease in the expression of CD63 tetraspanin protein elevates invasive potential of human melanoma cells", Experimental and Molecular Medicine, 35(4):317-323 (Aug. 2003).
S. Lebel-Binay et al, "CD82, member of the tetra-span-transmembrane protein family, is a costimulatory protein for T cell activation", J. Immunol., 155:101-110 (1995).
C. Huang et al, "Correlation of reduction in MRP-1/CD9 and KAI1/CD82 expression with recurrences in breast cancer patients", Am J Pathol, 153(3):973-983 (Sep. 1998).
P. Peters et al, "Cytotoxic T lymphocyte granules are secretory lysosomes, containing both perforin and granzymes", J. Exp. Med., 173:1099-1109 (May 1991).
B. Mannion et al, "Transmembrane-4 superfamily proteins CD81 (TAPA-1), CD82, CD63, and CD53 specifically associate with integrin alpha4beta1 (CD49d/CD29)", J. Immunol., 157:2039-2047 (1996).
Y. Koyama et al, "CD63, a member of tetraspan transmembrane protein family, induces cellular spreading by reaction with monoclonal antibody on substrata", Biochem Biophys Res Comm, 246(3):841-846 (1998).
K. Radford et al, "Regulation of tumor cell motility and migration by CD63 in a human melanoma cell line", J. Immunol., 158:3353-3358 (1997).
J. Li et al, "Recombinant CD63/ME491/neuroglandular/NKI/C-3 antigen inhibits growth of established tumors in transgenic mice", J. Immunol., 171:2922-2929 (2003).
M. Metzelaar et al, "CD63 antigen", J. Biol. Chem., 266(5):3239-3245 (Feb. 1991).
A. Zannettino et al, "A powerful new technique for isolating genes encoding cell surface antigens using retroviral expression cloning", J. Immunol., 156:611-620 (1996).
V. Toothill et al, "Characterization of the enhanced adhesion of neutrophil leukocytes to thrombin-stimulated endothelial cells", J. Immunol., 145(1):283-291 (Jul. 1990).
T. Kobayashi et al, "The tetraspanin CD63/lamp3 cycles between endocytic and secretory compartments in human endothelial cells", Molecular Biology of the Cell, 11:1829-1843 (May 2000).
K. Skubitz et al, "CD63 associates with tyrosine kinase activity and CD11/CD18, and transmits an activation signal in neutrophils", J. Immunol., 157:3617-3626 (1996).
F. Berditchevski et al, "A novel between integrins, transmembrane-4 superfamily proteins (CD63 and CD81), and phosphatidylinositol 4-kinase", J. Biol. Chem., 272(5):2595-2598 (Jan. 1997).
F. Berditchevski et al, "Specific association of CD63 with the VLA-3 and VLA-6 integrins", J. Biol. Chem., 270(30):17784-17790 (Jul. 1995).
K. Skubitz et al, "CD63 associates with CD11/CD18 in large detergent-resistant complexes after translocation to the cell surface in human neutrophils", FEBS Letters, 469:52-56 (2000).
K. Radford et al, "CD63 associates with transmembrane 4 superfamily members, CD9 and CD81, and with beta1 integrins in human melanoma", Biochem Biophys Res Comm, 222:13-18 (1996).
C. Claas et al, "Evaluation of prototype transmembrane 4 superfamily protein complexes and their relation to lipid rafts", J. Biol. Chem., 276(11):7974-7984 (Mar. 2001).
C. Hammond et al, "The tetraspan protein CD82 is a resident of MHC class II compartments where it associates with HLA-DR, -DM, and -DO molecules", J. Immunol, 161:3282-3291 (1998).
D. Demetrick et al, "ME491 melanoma-associated glycoprotein family: antigenic identity of ME491, NKI/C-3, neuroglandular antigen (NGA), and CD63 proteins", J. Natl. Cancer Inst, 84(6):422-429 (Mar. 1992).
C. Vennegoor et al, "Circulating melanoma-associated antigen detected by monoclonal antibody NKI/C-3", Cancer Immunol Immunother, 23:93-100 (1986).
M. Wang et al, "An ocular melanoma-associated antigen", Arch Ophthalmol., 110:399-404 (1992).
B. Ulbricht et al, "Influence of 12(S)-hydroxyeicosatetraenoic acid (12(S)-HETE) on the localization of cathepsin B and cathepsin L in human lung tumor cells", Eur J Cell Biol, 74:294-301 (Nov. 1997).
M. Barrio et al, "Monoclonal antibody FC-5.01, directed against CD63 antigen, is internalized into cytoplasmic vesicles in the IIB-BR-G human breast cancer cell line", Hybridoma, 17(6):517-523 (1998).
M. Adachi et al, "Novel staging protocol for non-small-cell lung cancers according to MRP-1/CD9 and KAII/CD82 gene expression", J. Clin. Oncol., 16(4):1397-1406 (Apr. 1998).
E. Rubinstein et al, "CD9, CD63, CD81, and CD82 are components of a surface tetraspan network connected to HLA-DR and VLA integrins", Eur. J. Immunol., 26:2657-2665 (1996).
H. Hotta et al, "Genomic structure of the ME491/CD63 antigen gene and functional analysis of the 5'-flanking regulatory sequences", Biochem Biophys Res Comm, 185(1):436-442 (May 1992).
Y. Koyama et al, "A novel monoclonal antibody induces the differentiation of monocyte leukemic cells", Biochem Biophys Res Comm, 168(3):898-904 (May 1990).
A. Carmo et al, "Association of the transmembrane 4 superfamily molecule CD53 with a tyrosine phosphatase activity", Eur. J. Immunol., 25:2090-2095 (1995).
M. Barrio et al, "A new epitope on human melanoma-associated antigen CD63/ME491 expressed by both primary and metastatic melanoma", Hybridoma, 17(4):355-364 (1998).
Z. Si et al, "Expression of the neuroglandular antigen and analogues in melanoma, CD9 expression appears inversely related to metastatic potential of melanoma", Int. J. Cancer, 54:37-43 (1993).
K. Radford et al, "Suppression of human melanoma cell growth and metastasis by the melanoma-associated antigen CD63 (ME491)", Int. J. Cancer, 62:631-635 (1995).
L. Sikora et al, "Characterization of a novel neuroglandular antigen (NGA) expressed on abnormal human melanocytes", Int. J. Cancer, 39:138-145 (1987).
S. Kennel et al, "Monoclonal antibody to rat CD63 detects different molecular forms in rat tissue", Hybridoma, 17(6):509-515 (1998).
H. Hotta et al, "Molecular cloning and characterization of an antigen associated with early stages of melanoma tumor progression", Cancer Research, 48:2955-2962 (Jun. 1988).
H. Nieuwenhuis et al, "Studies with a monoclonal antibody against activated platelets: evidence that a secreted 53,000-molecular weight lysosome-like granule protein is exposed on the surface of activated platelets in the circulation", Blood, 70(3):838-845 (Sep. 1987).
B. Atkinson et al, "Monoclonal antibody to a highly glycosylated protein reacts in fixed tissue with melanoma and other tumors", Hybridoma, 4(3):243-255 (1985).

G. Sauer et al, "Expression of tetraspanin adaptor proteins below defined threshold values is associated with in vitro invasiveness of mammary carcinoma cells", Oncology Reports, 10:405-410 (2003).

H. Hotta et al, "Overexpression of the human melanoma-associated antigen ME491 patially suppresses in vivo malignant phenotypes of H-ras-transformed NIH3T3 cells in athymic nude mice", Melanoma Research, 1:125-132 (1991).

M. Kondoh et al, "Decreased expression of human melanoma-associated antigen ME491 along the progression of melanoma pre-canceroses to invasive and metastatic melanomas", Melanoma Research, 3:241-245 (1993).

* cited by examiner

Figure 5

| ProFound - Search Result Summary | | | | |
|---|---|---|---|---|
| Protein Candidates for search B9D1575B-060C-21722561 [96146 sequences searched] | | | | |
| Rank | Probability | Est'd Z | Protein Information and Sequence Analyse Tools (T) | kDa |
| +1 | 7.6e-001 | 0.55 | CD63 antigen; melanoma 1 antigen; ocular melanoma-associated antigen; melanoma-associated antigen ME491; lysosome-associated membrane glycoprotein 3; granulophysin; melanoma-associated antigen MLA1 [Homo sapiens] | 26.47 |

Figure 11
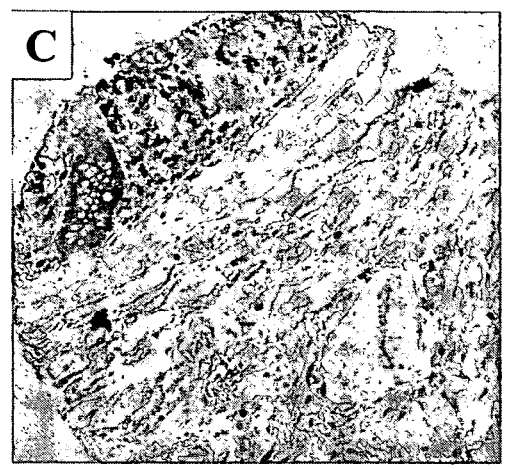
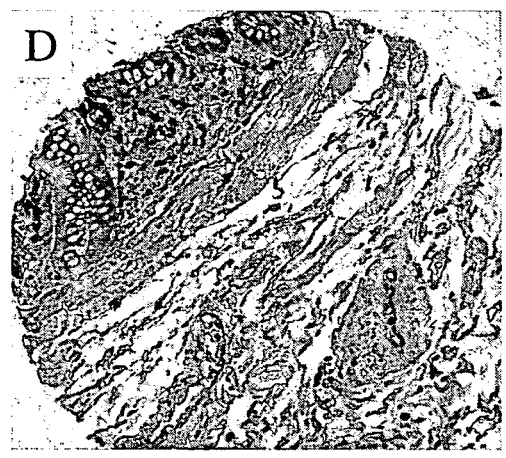

Figure 12
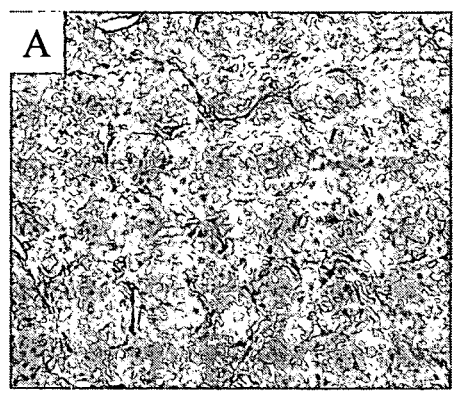
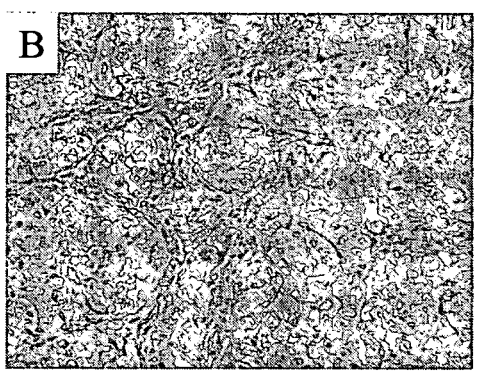
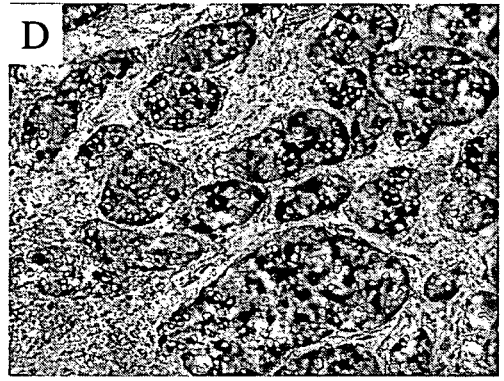

Figure 13
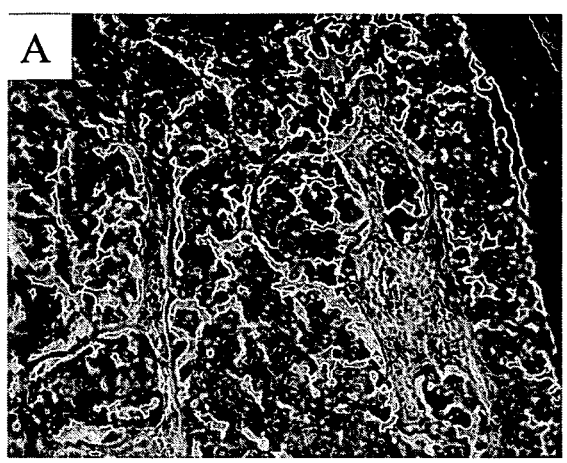

Figure 14

SEQUENCE LISTING

<160> NUMBER OF SEQ ID NOS: 5

<210> SEQ ID NO 1
<211> LENGTH: 30
<212> TYPE: DNA
<213> ORGANISM: Artificial
<220> FEATURE:
<223> OTHER INFORMATION: primer sequence used for PCR

<400> SEQUENCE: 1
gccgtgggat ccggggcaca gcttgtcctg                30

<210> SEQ ID NO 2
<211> LENGTH: 33
<212> TYPE: DNA
<213> ORGANISM: Artificial
<220> FEATURE:
<223> OTHER INFORMATION: primer sequence used for PCR

<400> SEQUENCE: 2
gatgacgaat tctcacagag agccaggggt agc             33

<210> SEQ ID NO 3
<211> LENGTH: 27
<212> TYPE: DNA
<213> ORGANISM: Artificial
<220> FEATURE:
<223> OTHER INFORMATION: primer sequence used for PCR

<400> SEQUENCE: 3
ggctatggat ccagagataa ggtgatg                    27

<210> SEQ ID NO 4
<211> LENGTH: 30
<212> TYPE: DNA
<213> ORGANISM: Artificial
<220> FEATURE:
<223> OTHER INFORMATION: primer sequence used for PCR

<400> SEQUENCE: 4
taccagaatt caatttttcc tcagccagcc                 30

<210> SEQ ID NO 5
<211> LENGTH: 10
<212> TYPE: PRT
<213> ORGANISM: Homo sapiens

<400> SEQUENCE: 5

Val Met Ser Glu Phe Asn Asn Asn Phe Arg
1               5                   10

CYTOTOXICITY MEDIATION OF CELLS EVIDENCING SURFACE EXPRESSION OF CD63

REFERENCE TO RELATED APPLICATIONS

This application is a continuation-in-part of application Ser. No. 10/603,006, filed Jun. 23, 2003, which is a continuation-in-part of application Ser. No. 10/348,231, filed Jan. 21, 2003 issued as U.S. Pat. No. 7,009,040, the contents of each of which are herein incorporated by reference.

FIELD OF THE INVENTION

This invention relates to the diagnosis and treatment of cancerous diseases, particularly to the mediation of cytotoxicity of tumor cells; and most particularly to the use of cancerous disease modifying antibodies (CDMAB), optionally in combination with one or more chemotherapeutic agents, as a means for initiating the cytotoxic response. The invention further relates to binding assays, which utilize the CDMAB of the instant invention.

BACKGROUND OF THE INVENTION

CD63 is a Type III membrane protein of the tetraspanin family whose 20 current members are characterized by the presence of four transmembrane segments. Several groups independently identified CD63, using antibodies raised to whole cell preparations of activated platelets, granulocytes, and melanoma cells. Cloning of the respective cDNAs of their cognate glycoprotein antigens led to the recognition that the different antigens were one and the same molecule. The Sixth International Workshop on Leukocyte Typing (1996) subsequently categorized these antibodies as CD63 antibodies. Prior to the 1996 Workshop, CD63 was known by multiple names (melanoma 1 antigen, ocular melanoma-associated antigen, melanoma associated antigen ME491, lysosome-associated membrane glycoprotein 3, granulophysin, melanoma-associated antigen MLA1), which were sometimes related to the antibodies that led to its partial characterization and identification. Thus, CD63 was also designated as antigen ME491 (MAb ME491), neuroglandular antigen (MAbs LS59, LS62, LS76, LS113, LS140 and LS152), Pltgp40 (MAbs H5C6, H4F8 and H5D2), human bone marrow stromal cell antigen (MAb 12F12), osteoprogenitor-specific marker (MAb HOP-26), and integrin-associated protein (MAb 6H1). Other antibodies that were found to cross react with human CD63 were 8-1H, 8-2A (cross-reactivity with ME491), NKI/C-3 and NKI/black-13 (Vannegoor and Rumke, 1986; Demetrick et al., 1992; Wang et al., 1992).

CD63 was initially cloned from a melanoma cDNA library using MAb ME491, one of a number of antibodies raised against a preparation of human melanoma cells. It was shown that the reactivity of MAb ME491 appeared to be inversely correlated with melanoma progression in a study of human melanoma biopsies. The reactivity of the ME491 antibody was low in normal melanocytes, higher in the early stages of melanoma progression (dysplastic nevi and radial growth phase (RGP) tumors) and decreased or even absent in more advanced melanoma tumors such as those in the vertical growth phase (VGP) and in metastatic tumors.

CD63 was also found and partially characterized in human platelets using MAb 2.28 (raised against activated platelets) that detected an activation-dependent platelet membrane 53 kDa glycoprotein. This molecule was also associated with the membrane of internal granules in unstimulated platelets. In the same study MAb 2.28 also labelled internal granules in megakaryocytes and endothelial cells, where it co-localized with antibodies to the enzyme cathepsin D, a known marker of lysosomal compartments. Follow up studies with antibody clustering and expression cloning, led to the identification of the antigen recognized by this antibody as CD63, and further confirmed its presence in lysosomal compartments, where it co-localized with the compartment-specific markers LAMP-1 and LAMP-2. Cloning of this molecule identified it as CD63 and allowed its inclusion in the tetraspanin family.

Expression of CD63 was detected in many different tissues and cell types. At the cellular level it was found to be associated with the plasma membrane and also with intracellular late endosomal vesicular structures. Cell activation led, in certain cases, to increased surface expression by mobilization of intracellular stores of CD63. CD63 was also found to co-localize, and physically associate, with MHC class II in B-lymphocytes, particularly in endosomes, in exosomes involved in exporting MHC class II complexes to the surface, and in secreted vesicles. CD63 was found to interact with other members of the tetraspanin family, such as CD9, CD81, CD 11 (integrin chain $\alpha_{M,L,X}$), CD 18 (integrin chain $\beta_2$), CD49c (VLA-3 or integrin chain $\alpha_3$), CD49d (integrin chain $\alpha_4$), CD49f (VLA-6 or integrin chain $\alpha_6$) and CD29 (integrin chain $\beta_1$), in a variety of cell types including B- and T-lymphocytes, neutrophils, breast cancer and melanoma cells.

The role of CD63 in cancer has been unclear. Although CD63 was initially discovered by several independent groups to be involved in diverse events such as platelet and granulocyte activation, MHC class II-dependent antigen presentation, integrin-dependent cell adhesion and motility, and tumor progression in certain types of cancers, its function has yet to be fully elucidated. Even though current evidence supports its role in a variety of cellular physiological events, it is not clear if these functions are independent of each other or if there is an underlying common cellular mechanism in which CD63 is involved.

Several groups have investigated the association between CD63 and the progression of certain types of tumors, particularly melanomas. A number of other anti-CD63 monoclonal antibodies, in addition to Mab ME491, were developed for immunohistochemical (IHC) staining of cancer samples obtained from patients with tumors at various stages of progression. It was observed that decreased staining, interpreted by the authors as most likely reflecting decreased expression of CD63, correlated with advanced progression and with metastatic characteristics of the tumors. A more recent study, also described a significant correlation between the apparent decreased expression levels (after quantitation of mRNA) of several members of the tetraspanin protein family, including CD63, and the in vitro invasiveness of several mammary carcinoma-derived cell lines. Another study identified CD63, by differential display, in cultured breast cancer cells subjected to estrogen deprivation. This indicated that CD63 expression can be steroid-hormone regulated and that altered CD63 abundance and/or function might also be associated with breast tumor progression.

By contrast, work with anti-CD63 monoclonal antibody MAb FC-5.01 revealed that its reactive epitope was variably expressed in different normal tissues. Although this antibody was found to recognize CD63, it did not distinguish between early and more advanced stage melanomas, including metastatic melanomas (unlike MAb ME491), which suggested that the CD63 antigen was present in these more advanced tumors, but that some of its epitopes may have been masked in the cells from tumors at different stages. This might have been due to altered post-translational modifications of the core CD63 polypeptide, or to the interaction of CD63 with other molecules, which might have affected the availability of specific epitopes for antibody recognition and binding. These results supported the observation, described by Si and Hersey (1993), that staining with the anti-CD63 MAb NKI-C3, did not distinguish between tissue sections from melanomas at different stages of progression, such as primary, radial growth phase, vertical growth phase, and metastatic melanomas. Although in other studies (Adachi et al., 1998; Huang et al., 1998) analysis of mRNA from breast, and from non-small-cell lung cancers, by quantitative PCR, revealed that for two tetraspanin family members (CD9 and CD82) there was a significant correlation between their expression levels and tumor progression and patient prognosis, no such correlation was found for CD63, in that its expression was similar in all the samples. As a result of these, apparently conflicting, results, there is lack of strong and consistent data that would definitively demonstrate the association of CD63 with cancer.

To date very few in vivo studies have attempted to establish a link between CD63 and an eventual tumor suppressor function of this molecule. In one of these studies, human CD63-overexpressing H-ras-transformed NIH-3T3 cells, injected both subcutaneously and intraperitoneally into athymic mice, revealed a decreased malignant/tumorigenic phenotype, as indicated by decreased tumor size and metastatic potential as well as by increased survival time, when compared to the behavior of the parental non-CD63-overexpressing cells. This suggested that the presence of human CD63 in the transformed cells might suppress their malignant behavior. More recently, work with a transgenic mouse model expressing human CD63, and developed to induce tolerance to CD63, indicated that tumor growth of an injected human CD63-MHC class I ($H-2K^b$) co-transfected murine melanoma cell line could be inhibited, and survival increased, upon immunization with human CD63 fused to vaccinia virus. It was suggested by the authors that the therapeutic effect was T-lymphocyte dependent, and that endogenous anti-CD63 antibodies did not appear to be involved in this protective effect, since tumor growth inhibition only occurred when animals were injected with the CD63-MHC class I co-transfected cells and not with the CD63-only transfected cell line. This interpretation was supported by the fact that in wild type animals, pre-immunized with purified human CD63 and shown to have developed anti-human CD63 antibodies, there was no protective effect against tumor cell growth. Work described by Radford et al. (1995) using the KM3 cell line, initially thought to be of human origin but later characterized as being of rat lineage, transfected with human CD63, suggested that expression of this protein decreased the growth and metastastic potential of these cells, relative to that observed using the parental non-transfected KM3 cells, when injected intradermally into athymic mice, although there was no significant difference between the in vitro growth rates of the various transfected and non-transfected cell lines. These observations distinguished the potential effect of CD63 from that of other tumor suppressor genes known to affect both the in vivo and the in vitro growth rates of tumor cells. Furthermore, addition of the anti-CD63 monoclonal antibody ME491, which was found to have a functional effect on the same cells by decreasing their random motility in an in vitro assay (Radford et al., 1997), did not impact their in vitro growth rates.

This study also described the observation that CD63 may promote migration in response to extracellular matrix (ECM)-derived chemoattractants, such as laminin, fibronectin, collagen and vitronectin, and that this effect may be mediated by the functional involvement of $\beta_1$-type integrins, although antibodies to the integrins were unable to block these effects. However, there appeared to be an antagonistic effect between the role of vitronectin-mediated signaling (a known ligand for the integrin $\alpha_v\beta_5$) and that of the signaling mediated by other ECM components such as fibronectin, laminin and collagen on CD63 transfected cells. This suggested that under specific conditions, in the presence of ECM components, expression of CD63 may lead to decreased migration, and that this may be dependent on a fine balance between adhesion and motility. In another study, an anti-CD63 monoclonal antibody (MAb 710F) enhanced the adhesion and spreading of PMA-treated HL-60 cells, while another anti-CD63 monoclonal antibody (MAb 2.28), promoted a similar effect, but only on a much smaller fraction of the cell population, and only when added in much larger amounts. These results showed that although many antibodies to CD63 have been developed, their functional effects can be quite different.

Tetraspanins may also be involved in cell proliferation. Oren et al. (1990) described anti-proliferative effects of the murine MAb 5A6, that recognizes CD81 (TAPA-1), on lymphoma cell lines. In another study, ligation of CD37 in human T-lymphocytes with antibodies blocked CD37-induced proliferation. More recently, a study with an animal model deficient in the expression of CD37 (CD37 knockout) revealed that T lymphocytes from this animal were hyperproliferative compared to those from wild type animals in response to concanavalin A activation and CD3/T cell receptor engagement. It was therefore proposed that a functional role in cell growth and proliferation might be a common feature of the tetraspanin family. Recent studies with hepatoblastoma and hepatocellular carcinoma cells revealed that engagement of these cells with anti-CD81 monoclonal antibodies led to activation of the Erk/MAP kinase pathway. This signaling pathway has been shown to be involved with cell growth and proliferation events. In parallel work, transfected cell lines overexpressing human CD81 displayed increased proliferation relative to the mock-transfected control cells. Therefore, available evidence has pointed to a role of the tetraspanins in general, and of CD63 in particular, in events associated with cell growth proliferation and with cell adhesion/motility. These two types of cellular events are currently the target of intense research as both play a central role in tumor progression and metastasis.

Until now, no anti-CD63 antibodies, or other reagents that specifically targeted CD63-expressing cells, were reported and shown to have a simultaneous impact on the in vitro and on the in vivo growth characteristics of tumor cells, and also on the survival time of animal models of tumor cell growth.

Amino acid sequence determination and analysis did not reveal homology between tetraspanins and other protein families, or with any previously characterized functional modules, nor has it suggested any previously known enzymatic activity. As a result it has been very difficult to investigate the role of this family of proteins in the modulation of signal transduction pathways. However, the evidence generated using tetraspanin-specific reagents that led to changes in cellular physiology, and which were intimately dependent on the modulation of signal transduction pathways, suggests that tetraspanins have signal transduction properties. CD63 was shown to associate, both physically and functionally, with a number of molecules that are themselves either enzymes involved in the generation of secondary messenger signals, or are associated physically and/or functionally with such enzymes.

Experiments designed to dissect the mechanism controlling the interaction of human neutrophils with endothelial cells, which is one of the initial steps of the inflammatory response, revealed that pre-treatment of neutrophils with several anti-CD63 monoclonal antibodies (AHN-16, AHN-16.1, AHN-16.2, AHN-16.3 and AHN-16-5) promoted their adhesion to cultured endothelial cell layers. Furthermore this effect was strongly dependent on the presence of calcium ion ($Ca^{2+}$), a well-known modulator of many intracellular signaling pathways and which was restricted to a specific period of time during which the cells were exposed to the stimulating antibodies. After longer exposure to the antibody, adhesion of the neutrophils to the endothelial cells became insensitive to the later addition of $Ca^{2+}$, therefore implicating a dynamic and temporally regulated (transitory) event. In addition, CD63 was found to physically interact with the CD11/CD18 protein complex, and reagents that specifically targeted this complex mediated a modulatory signal. In this study CD63 was also found to be physically associated with, or to be part of, a complex that included the enzyme tyrosine kinases Lck and Hck. These enzymes are members of a class of proteins that play a central role in mediating intracellular regulatory signals upon activation of specific surface receptors and are part of cascades of signaling pathways that result in cell-specific physiological changes. Another study suggested that co-ligation of tetraspanins (including CD63) with monoclonal antibodies could enhance the phosphorylation or activity of the enzyme focal adhesion kinase (FAK) that was induced by adhesion of MDA-MB-231 breast cancer cells to collagen substrate. This pointed to a direct involvement of CD63 (and of other tetraspanin family members) in the modulation of integrin-mediated tyrosine kinase signaling pathways. Other signaling pathways that may functionally intersect with the presence and ligation of surface CD63 by the anti-CD63 monoclonal antibody MAb 710F appear to be those dependent on modulation of phosphorylation by the enzyme protein kinase C (PKC), another well known modulator of intracellular signaling pathways. In this context, enhancement of adhesion and of morphological changes in the myeloid cell line HL-60 by MAb 710F was dependent on pre-treatment of the cells with phorbol myristate acetate (PMA) although the temporal involvement of PKC was not conclusively demonstrated. However, later work by an independent group demonstrated that PMA-induced HL-60 differentiation was PKC-activity dependent since the molecule Ro31-8220, a specific inhibitor of this enzyme, blocked the effect of PMA.

Further evidence supporting the association of CD63, and other tetraspanin family members, with signal transduction pathways, arose from work that described a physical association, either direct or as part of a supramolecular complex, between CD63 (and also CD53) molecules with tyrosine phosphatase activity. In this study, immunoprecipitate complexes isolated with anti-CD63 antibodies were shown to be associated with tyrosine phosphatase activity, although unlike for CD53, which was shown to associate with the tyrosine phosphatase CD45, it was not possible to identify the CD63-associated phosphatase. More recently several members of the tetraspanin family were also found to be associated with a type II phosphatidylinositol 4-kinase (type II PI 4-K) (Berditchevski et al., 1997). This interaction appeared to be very specific since it was only identified for CD9, CD63, CD81, CD151 and A15/TALLA, and it was not observed to occur with CD37, CD52, CD82, or NAG-2. In addition, the association between tetraspanin family members and PI-4K was mutually exclusive since each PI-4 kinase-containing complex was limited to a single tetraspanin family member. CD63-PI-4 kinase complexes, in particular, were found, almost entirely, in intracellular compartments in lipid raft-like domains, unlike those formed with the other tetraspanin members. This observation suggested that this CD63 fraction, found to interact with the PI-4 kinase, might have been involved in specific intracellular events (Claas, C, et al., 2001) related to, or dependent from, phosphoinositide biosynthesis pathways, which are well known for their involvement in the regulation of membrane trafficking (endocytosis and exocytosis) and of cytoskeleton reorganization, in addition to their function as secondary messenger molecules (Martin, T., 1998).

The direct and important involvement of all the enzymes, that CD63 was found until now to be directly associated with, in the regulation of signaling pathways provided further evidence in support of the association of CD63 with the modulation of signal transduction pathways, either as a regulator or as an effector molecule downstream from the activity of these enzymes.

Elucidation of the mechanisms that lead to tumor progression is a very difficult and complex endeavor frequently marked by apparently contradictory observations and, as a result, it rare that those observations successfully translate into effective therapies. In view of what is currently known about the association of CD63 with tumor progression and metastasis and with signal transduction mechanisms, it is possible that its function may be altered, in tumor cells.

Development of antigen-specific reagents with cytotoxic effects on tumor cells, that bind cells expressing the recognized antigen(s) and which by themselves, or associated with other molecules, have cellular and in vivo physiological activity such that these reagents inhibit tumor cell growth, progression and metastasis, without significant deleterious effects on normal cell populations, would be extremely beneficial as a potential therapeutic and or diagnostic tool.

Prior Patents:

U.S. Pat. No. 5,296,348 teaches methods for selecting monoclonal antibodies specific for cancer cell surface antigens that are internalizing, and for identifying monoclonal antibodies having anti-transcriptional and/or anti-replicational effects on cell metabolism. By way of example the ME491 antibody was shown to internalize in W9, WM35, WM983 melanoma cells, and SW948 colorectal carcinoma cells. In addition ME491 antibody was shown to decrease transcription and cell proliferation in SW948 cells. The patent application US20030211498A1 (and its related applications: WO0175177A3, WO075177A2, AU0153140A5) allege a method of inhibiting the growth or metastasis of an ovarian tumor with an antibody that binds an ovarian tumor marker polypeptide encoded by an ovarian tumor marker gene selected from among a group that includes CD63 antigen. Serial analysis of gene expression using ovarian cancer was carried out to identify ovarian tumor marker genes which lead to the identification of CD63 as a candidate. The patent application WO0205555 A1 (and its related application CN1364803A) alleges a new polypeptide-human CD63 antigen 56.87. The patent application CN1326962A alleges a new polypeptide-human CD63 antigen 14.63. The patent application CN1326951A alleges a new polypeptide-human CD63 antigen 15.07. The patent application CN1351054A alleges a new polypeptide-human CD63 antigen 11.11. These patents and patent applications identify CD63 antigens and antibodies but fail to disclose the isolated monoclonal antibody of the instant invention, or the utility of the isolated monoclonal antibody of the instant invention.

SUMMARY OF THE INVENTION

The instant inventors have previously been awarded U.S. Pat. No. 6,180,357, entitled "Individualized Patient Specific Anti-Cancer Antibodies" directed to a process for selecting individually customized anti-cancer antibodies, which are useful in treating a cancerous disease. For the purpose of this document, the terms "antibody" and "monoclonal antibody" (mAb) may be used interchangeably and refer to intact immunoglobulins produced by hybridomas (e.g. murine or human), immunoconjugates and, as appropriate, immunoglobulin fragments and recombinant proteins derived from said immunoglobulins, such as chimeric and humanized immunoglobulins, F(ab') and F(ab')$_2$ fragments, single-chain antibodies, recombinant immunoglobulin variable regions (Fv)s, fusion proteins etc. It is well recognized in the art that some amino acid sequence can be varied in a polypeptide without significant effect on the structure or function of the protein. In the molecular rearrangement of antibodies, modifications in the nucleic or amino acid sequence of the backbone region can generally be tolerated. These include, but are not limited to, substitutions (preferred are conservative substitutions), deletions or additions. Furthermore, it is within the purview of this invention to conjugate standard chemotherapeutic modalities, e.g. radionuclides, with the CDMAB of the instant invention, thereby focusing the use of said chemotherapeutics. The CDMAB can also be conjugated to toxins, cytotoxic moieties, enzymes e.g. biotin conjugated enzymes, or hematogenous cells, thereby forming an antibody conjugate.

This application utilizes the method for producing patient specific anti-cancer antibodies as taught in the '357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies and/or a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

Using substantially the process of U.S. Pat. No. 6,180,357, and as disclosed in Ser. No. 10/348,231, the mouse monoclonal antibody 7BD-33-11A was obtained following immunization of mice with cells from a patient's breast tumor biopsy. The 7BD-33-11A antigen was expressed on the cell surface of a wide range of human cell lines from different tissue origins. The breast cancer cell line MCF-7 and prostate cancer cell line PC-3 were susceptible to the cytotoxic effects of 7BD-33-11A in vitro.

The result of 7BD-33-11A cytotoxicity against breast and prostate cancer cells in culture was further extended by its anti-tumor activity towards these cancer indications in vivo (as disclosed in Ser. No. 10/348,231 and Ser. No. 10/603, 006). Pre-clinical xenograft tumor models are considered valid predictors of therapeutic efficacy.

As outlined and described in Ser. No. 10/348,284 and Ser. No. 10/603,006, 7BD-33-11A prevented tumor growth and tumor burden in a preventative in vivo model of human breast cancer. Monitoring continued past 300 days post-treatment. 7BD-33-11A never developed tumors and 87.5 percent of the 7BD-33-11A treatment group was still alive at over 9 months post-implantation. Conversely, the isotype control group had 100 percent mortality by day 72 (23 days post-treatment). Therefore 7BD-33-11A enhanced survival and prevented tumor growth (thus delaying disease progression) in a breast cancer model.

Also as outlined and described in Ser. No. 10/348,284 and Ser. No. 10/603,006, 7BD-33-11A significantly suppressed tumor growth and decreased tumor burden in an established in vivo model of human breast cancer. By day 80 (23 days post-treatment), 7BD-33-11A treated mice had 83 percent lower mean tumor volumes in comparison to the isotype control group (p=0.001). Using survival as a measure of antibody efficacy, it was estimated that the risk of dying in the 7BD-33-11A treatment group was about 16 percent of the isotype control group (p=0.0006) at around 60 days post-treatment. 100 percent of the isotype control group died by 50 days post-treatment. In comparison, 60 percent of the 7BD-33-11A treatment groups were still alive at 130 days post-treatment. This data demonstrated that 7BD-33-11A treatment conferred a survival benefit and reduced tumor burden compared to the control treated group. 7BD-33-11A treatment appeared safe, as it did not induce any signs of toxicity, including reduced body weight and clinical distress. Thus, 7BD-33-11A treatment was efficacious as it both delayed tumor growth and enhanced survival compared to the control-treated groups in a well-established model of human breast cancer.

The effect of 7BD-33-11A compared to a chemotherapeutic drug (Cisplatin) treatment alone or in combination was determined in two different established breast cancer xenograft models. In the MDA-MB-231 (MB-231) model, at day 69 (5 days after treatment), 7BD-33-11A treatment resulted in a 76 percent reduction in tumor growth relative to the buffer control treated animals (p<0.001). Cisplatin treatment alone or in combination with 7BD-33-11A resulted in a 79 and 86 percent reduction in tumor size, respectively, relative to the control (p<0.001). In the MDA-MB-468 (MB-468) model, at day 55 (5 days after treatment) Cisplatin treatment alone and in combination with 7BD-33-11A showed the greatest reduction in tumor growth, 95 percent (p=0.024) and 97 percent (p=0.17) respectively. Also at day 55, 7BD-33-11A treatment alone showed a reduction in tumor growth by 37 percent (p=0.3958), in comparison to the buffer control. In both the MB-231 and MB-468 model, treatment with 7BD-33-11A led to greater animal well-being in comparison to treatment with Cisplatin as measured by body weight. These results indicate that 7BD-33-11A treatment has greater efficacy in comparison to Cisplatin treatment alone in the MB-231 model and was better tolerated with fewer adverse effects, such as weight loss, than Cisplatin in both breast cancer models.

To determine the efficacious effects of 7BD-33-11A treatment at various doses, a dose response experiment was performed in a preventative breast cancer xenograft model. At day 55 (5 days after treatment), the 0.2 mg/kg treatment group had prevented tumor growth by 85 percent relative to the isotype control treated group. Also at day 55, both the 2 and 20 mg/kg treatment groups had yet to develop tumors. Similar results were obtained past day 125 (75 days after treatment), where the 20 mg/kg treatment group had still not developed tumors and the 2 mg/kg treatment group had some initial tumor growth. 7BD-33-11A treatment also demonstrated a survival benefit. All of the mice in the isotype control group had died by day 104 (54 days after treatment) while the 0.2 mg/kg 7BD-33-11A treatment group survived until day 197 (147 days after treatment). Even greater survival benefits were observed with the 2.0 and 20 mg/kg 7BD-33-11A treatment groups; only 50 percent of the 2.0 mg/kg treatment group had died by day 290 (240 days after treatment) while none of the 20 mg/kg treatment group had died by also day 290. Therefore, 7BD-33-11A treatment showed significant tumor growth reduction and increased survival with all three doses with the greatest degree of efficacy being exhibited by the highest dose.

In addition to the beneficial effects in the established in vivo tumor model of breast cancer, 7BD-33-11A treatment also had anti-tumor activity against PC-3 cells in a preventative in vivo prostate cancer model (outlined in Ser. No. 10/603,006). 7BD-33-11A treatment was significantly ($p=0.001$) more effective in suppressing tumor growth shortly after the treatment period than an isotype control antibody. At the end of the treatment phase, mice given 7BD-33-11A had tumors that grew to only 31 percent of the isotype control group. For PC-3 SCID xenograft models, body weight can be used as a surrogate indicator of disease progression. On day 52, 7BD-33-11A treatment significantly ($p=0.002$) prevented the loss of body weight by 54 percent in comparison to isotype control. Mice were monitored for survival post-treatment. At 11 days post-treatment, isotype and buffer control mice had reached 100 percent mortality. Conversely, 7BD-33-11A reached 100 percent mortality at day 38 post-treatment, 3 times longer than the control groups. Thus, 7BD-33-11A treatment was efficacious as it both delayed tumor growth, prevented body weight loss and extended survival compared to the isotype control treated group in a well-established model of human prostate cancer.

In addition to the preventative in vivo tumor model of prostate cancer, 7BD-33-11A demonstrated anti-tumor activity against PC-3 cells in an established in vivo tumor model (outlined in Ser. No. 10/603,006). Treatment with 7BD-33-11A was again compared to isotype control. It was shown that the 7BD-33-11A treatment group had significantly ($p<0.024$) smaller mean tumor volumes compared with the isotype control treated group immediately following treatment. 7BD-33-11A treatment mediated tumor suppression by 36 percent compared to the isotype control group. The anti-tumor activities of 7BD-33-11A, in several different cancer models, make it an attractive anti-cancer therapeutic agent.

In order to validate the 7BD-33-11A epitope as a drug target, the expression of 7BD-33-11A antigen in normal human tissues was previously determined (Ser. No. 10/603, 006). This work was extended by comparison with commercially available anti-CD63 antibodies (RFAC4 and H5C6). Results from tissue staining indicated that 7BD-33-11A again showed restricted binding to various cell types but had binding to infiltrating macrophages, lymphocytes, and fibroblasts. The RFAC4 and H5C6 antibodies showed a similar staining pattern in comparison to each other. However, the staining pattern of both RFAC4 and H5C6 was quite different than that observed with 7BD-33-11A. Specifically, both RFAC4 and H5C6 antibodies bound to a broader range of normal tissues, usually had higher staining intensity in tissues where 7BD-33-11A was also positive and bound not only to infiltrating macrophages, lymphocytes and fibroblasts but also to the epithelium in a majority of the tissues.

Localization of the 7BD-33-11A antigen and determining its prevalence within the population, such as among breast cancer patients, is important in assessing the therapeutic use of 7BD-33-11A and designing effective clinical trials. To address 7BD-33-11A antigen expression in breast tumors from cancer patients, tumor tissue samples from 50 individual breast cancer patients were previously screened for expression of the 7BD-33-11A antigen (Ser. No. 10/603, 006). Current work compared the staining of 7BD-33-11A to RFAC4 and H5C6 and to an anti-Her2 antibody (c-erbB-2). The results of the current study were similar to previous results and showed that 36 percent of tumor tissue samples stained positive for the 7BD-33-11A antigen while 94 and 85 percent of breast tumor tissues were positive for the H5C6 and RFAC4 epitope respectively. Expression of 7BD-33-11A within patient samples appeared specific for cancer cells as staining was restricted to malignant cells. In addition, 7BD-33-11A stained 0 of 10 samples of normal tissue from breast cancer patients while both H5C6 and RFAC4 stained 7 of 8 samples of normal breast tissue. Breast tumor expression of the 7BD-33-11A antigen appeared to be localized to the cell membrane and cytoplasm of malignant cells, making CD63 an attractive target for therapy. 7BD-33-11A expression was further evaluated based on breast tumor expression of the receptors for the hormones estrogen and progesterone, which play an important role in the development, treatment, and prognosis of breast tumors. There was a slight correlation between estrogen or progesterone receptor expression and expression of 7BD-33-11A; tissues with receptor expression had slightly higher 7BD-33-11A expression. When tumors were analyzed based on their stage, or degree to which the cancer advanced, results suggested a trend towards greater positive expression with higher tumor stage for 7BD-33-11A. Similar results were obtained with RFAC4. H5C6 also showed a very slight correlation with estrogen or progesterone receptor expression but there was no apparent correlation with tumor stage. However, for all three antibodies, the results were limited by the small sample size. In comparison to c-erbB-2, 7BD-33-11A showed a completely different staining profile where half of the breast tumor tissue samples that were positive for the 7BD-33-11A antigen were negative for Her2 expression indicating a yet unmet targeted therapeutic need for breast cancer patients. There were also differences in the intensity of staining between the breast tumor tissue sections that were positive for both 7BD-33-11A and Her2. The c-erbB-2 antibody also positively stained one of the normal breast tissue sections.

Localization of the 7BD-33-11A antigen and its prevalence within prostate cancer patients is important in assessing the benefits of 7BD-33-11A immunotherapy to patients with prostate cancer and designing effective clinical trials. To address 7BD-33-11A antigen expression in prostate tumors from cancer patients, tumor tissue samples from 51 individual prostate cancer patients were screened for expression of the 7BD-33-11A antigen. The results of the study showed that 88 percent of tissue samples stained positive for the 7BD-33-11A antigen. Although 7BD-33-11A stained the normal tissue sections with high intensity as well, there was a higher degree of membranous staining in the tumor tissue samples in comparison to the normal samples. There was one embryonal rhabdomyosarcroma tissue sample that did not stain for the 7BD-33-11A antigen. There also appeared to be no direct correlation between tumor stage and presence of the 7BD-33-11A antigen. However, the results were limited by the small sample size.

To further extend the potential therapeutic benefit of 7BD-33-11A, the frequency and localization of the antigen within various human cancer tissues was also previously determined (Ser. No. 10/603,006). Several cancer types, in addition to breast and prostate cancer, expressed the 7BD-33-11A antigen. The positive human cancer types included skin (1/2), lung (3/4), liver (2/3), stomach (4/5), thyroid (2/2), uterus (4/4) and kidney (3/3). Some cancers did not express the antigen; these included ovary (0/3), testis (0/1), brain (0/2) and lymph node (0/2). As with human breast and prostate cancer tissue, localization of 7BD-33-11A occurred both on the membrane and within the cytoplasm of these tumor cells. So, in addition to the 7BD-33-11A antibody binding to cancer cell lines in vitro, there is evidence that the antigen is expressed in humans, and on multiple types of cancers.

As outlined herein, additional biochemical data also indicate that the antigen recognized by 7BD-33-11A is CD63. This is supported by studies showing that two monoclonal antibodies (RFAC4 and H5C6), reactive against CD63, identify proteins that bound to 7BD-33-11A by immunoprecipitation. In addition, further bacterial expression studies elucidated that 7BD-33-11A bound to extracellular loop 2 of CD63. The 7BD-33-11A epitope was also distinguished by being conformation dependent. These IHC and biochemical results demonstrate that 7BD-33-11A binds to the CD63 antigen. Thus, the preponderance of evidence shows that 7BD-33-11A mediates anti-cancer effects through ligation of a unique conformational epitope present on CD63. For the purpose of this invention, said epitope is defined as a "CD63 antigenic moiety" characterized by its ability to bind with a monoclonal antibody encoded by the hybridoma cell line 7BD-33-11A, antigenic binding fragments thereof or antibody conjugates thereof.

In toto, this data demonstrates that the 7BD-33-11A antigen is a cancer associated antigen and is expressed in humans, and is a pathologically relevant cancer target. Further, this data also demonstrates the binding of the 7BD-33-11A antibody to human cancer tissues, and can be used appropriately for assays that can be diagnostic, predictive of therapy, or prognostic. In addition, the cell membrane localization of this antigen is indicative of the cancer status of the cell due to the lack of expression of the antigen in most non-malignant cells, and this observation permits the use of this antigen, its gene or derivatives, its protein or its variants to be used for assays that can be diagnostic, predictive of therapy, or prognostic.

The present invention describes the development and use of 7BD-33-11A, developed by the process described in patent U.S. Pat. No. 6,180,357 and identified by, its effect, in a cytotoxic assay, in non-established and established tumor growth in animal models and in prolonging survival time in those suffering from cancerous disease. This invention represents an advance in the field of cancer treatment in that it describes, for the first time, a reagent that binds specifically to an epitope present on the target molecule, CD63, and that also has in vitro cytotoxic properties against malignant tumor cells but not normal cells, and which also directly mediates inhibition of tumor growth and enhancement of survival in in vivo models of human cancer. This is an advance in relation to any other previously described anti-CD63 antibody, since none have been shown to have similar properties. It also provides an advance in the field since it clearly demonstrates, and for the first time, the direct involvement of CD63 in events associated with growth and development of certain types of tumors. It also represents an advance in cancer therapy since it has the potential, to display similar anti-cancer properties in human patients. A further advance is that inclusion of this antibody in a library of anti-cancer antibodies will enhance the possibility of targeting tumors expressing different antigen markers by determination of the appropriate combination of different anti-cancer antibodies, to find the most effective in targeting and inhibiting growth and development of the tumors.

In all, this invention teaches the use of the 7BD-33-11A antigen as a target for a therapeutic agent, that when administered can reduce the tumor burden of a cancer expressing the antigen in a mammal, and can also lead to a prolonged survival of the treated mammal. This invention also teaches the use of a CDMAB (7BD-33-11A), and its derivatives, and antigen binding fragments thereof, to target its antigen to reduce the tumor burden of a cancer expressing the antigen in a mammal, and to prolong the survival of a mammal bearing tumors that express this antigen. Furthermore, this invention also teaches the use of detecting the 7BD-33-11A antigen in cancerous cells that can be useful for the diagnosis, prediction of therapy, and prognosis of mammals bearing tumors that express this antigen.

If a patient is refractory to the initial course of therapy or metastases develop, the process of generating specific antibodies to the tumor can be repeated for re-treatment. Furthermore, the anti-cancer antibodies can be conjugated to red blood cells obtained from that patient, or a compatible donor, and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and anti-cancer antibodies conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody-dependent cell-mediated cytotoxicity (ADCC) or complement-dependent cytotoxicity (CDC). For example murine IgM and IgG2a antibodies can activate human complement by binding the C-1 component of the complement system thereby activating the classical pathway of complement activation which can lead to tumor lysis. For human antibodies, the most effective complement-activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

Another possible mechanism of antibody-mediated cancer killing may be through the use of antibodies that function to catalyze the hydrolysis of various chemical bonds in the cell membrane and its associated glycoproteins or glycolipids, so-called catalytic antibodies.

There are two additional mechanisms of antibody-mediated cancer cell killing, which are more widely accepted. The first is the use of antibodies as a vaccine to induce the body to produce an immune response against the putative antigen that resides on the cancer cell. The second is the use of antibodies to target growth receptors and interfere with their function or to down regulate that receptor so that its function is effectively lost.

The clinical utility of a cancer drug is based on the benefit of the drug under an acceptable risk profile to the patient. In cancer therapy survival has generally been the most sought after benefit, however there are a number of other well-recognized benefits in addition to prolonging life. These other benefits, where treatment does not adversely affect survival, include symptom palliation, protection against adverse events, prolongation in time to recurrence or disease-free survival, and prolongation in time to progression. These criteria are generally accepted and regulatory bodies such as the U.S. Food and Drug Administration (F.D.A.) approve drugs that produce these benefits (Hirschfeld et al. Critical Reviews in Oncology/Hematolgy 42:137-143 2002). In addition to these criteria it is well recognized that there are other endpoints that may presage these types of benefits. In part, the accelerated approval process granted by the U.S. F.D.A. acknowledges that there are surrogates that will likely predict patient benefit. As of year-end (2003), there have been sixteen drugs approved under this process, and of these, four have gone on to full approval, i.e., follow-up studies have demonstrated direct patient benefit as predicted by surrogate endpoints. One important endpoint for determining drug effects in solid tumors is the assessment of tumor burden by measuring response to treatment (Therasse et al. Journal of the National Cancer Institute 92(3):205-216 2000). The clinical criteria (RECIST criteria) for such evaluation have been promulgated by Response Evaluation Criteria in Solid Tumors Working Group, a group of international experts in cancer. Drugs with a demonstrated effect on tumor burden, as shown by objective responses according to RECIST criteria, in comparison to the appropriate control group tend to, ultimately, produce direct patient benefit. In the pre-clinical setting tumor burden is generally more straightforward to assess and document. In that pre-clinical studies can be translated to the clinical setting, drugs that produce prolonged survival in pre-clinical models have the greatest anticipated clinical utility. Analogous to producing positive responses to clinical treatment, drugs that reduce tumor burden in the pre-clinical setting may also have significant direct impact on the disease. Although prolongation of survival is the most sought after clinical outcome from cancer drug treatment, there are other benefits that have clinical utility and it is clear that tumor burden reduction, which may correlate to a delay in disease progression, extended survival or both, can also lead to direct benefits and have clinical impact (Eckhardt et al. Developmental Therapeutics: Successes and Failures of Clinical Trial Designs of Targeted Compounds; ASCO Educational Book, 39$^{th}$ Annual Meeting, 2003, pages 209-219).

Accordingly, it is an objective of the invention to utilize a method for producing cancerous disease modifying antibodies from cells derived from a particular individual which are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach CDMAB and antigen binding fragments thereof.

It is a further objective of the instant invention to produce CDMAB whose cytotoxicity is mediated through ADCC.

It is yet an additional objective of the instant invention to produce CDMAB whose cytotoxicity is mediated through CDC.

It is still a further objective of the instant invention to produce CDMAB whose cytotoxicity is a function of their ability to catalyze hydrolysis of cellular chemical bonds.

A still further objective of the instant invention is to produce CDMAB which are useful in a binding assay for diagnosis, prognosis, and monitoring of cancer.

Other objects and advantages of this invention will become apparent from the following description wherein, by way of illustration and example, certain embodiments of this invention are set forth.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 5. Profound search summary table.

FIG. 11. Representative micrographs showing the binding pattern obtained with 7BD-33-11A (A), isotype negative control (B), anti-CD63 (RFAC4) antibody or the anti-CD63 (H5C6) antibody (D) on tissues sections of colon from a normal human tissue array. 7BD-33-11A, RFAC4 and H5C6 displayed positive staining for macrophages and lymphocytes at the lamina propria. RFAC4 and H5C6 also displayed strong staining for the mucosal epithelieum. Magnification is 200×.

FIG. 12. Representative micrographs showing the binding pattern obtained with 7BD-33-11A (A), isotype negative control (B), anti-CD63 (RFAC4) antibody or the anti-CD63 (H5C6) antibody (D) on tissues sections of infiltrative ductal carcinoma from a human breast cancer tissue array. 7BD-33-11A displayed weaker positive staining for the tumor cells in comparison to either RFAC4 or H5C6 antibody. Magnification is 200×.

FIG. 13. Representative micrographs showing the binding pattern obtained with 7BD-33-11A (A) or the anti-Her2 (c-erbB-2) antibody (B) on tissues sections of infiltrative ductal carcinoma from a human breast cancer tissue array. 7BD-33-11A displayed strong positive staining for the tumor cells in comparison to the anti-Her2 antibody, which displayed negative staining. Magnification is 200×.

FIG. 14. Representative micrographs showing the binding pattern obtained with 7BD-33-11A on tissues sections of prostate adenocarinoma (A) or normal prostate (B) from a human prostate cancer tissue array. 7BD-33-11A displayed strong positive membranous staining for the tumor cells in the adenocarinoma tissue section. 7BD-33-11A showed both membranous and cytoplasmic staining of the glandular epithelium in the normal prostate tissue section. Magnification is 200×.

DETAILED DESCRIPTION OF THE INVENTION

EXAMPLE 1

Figure 1:
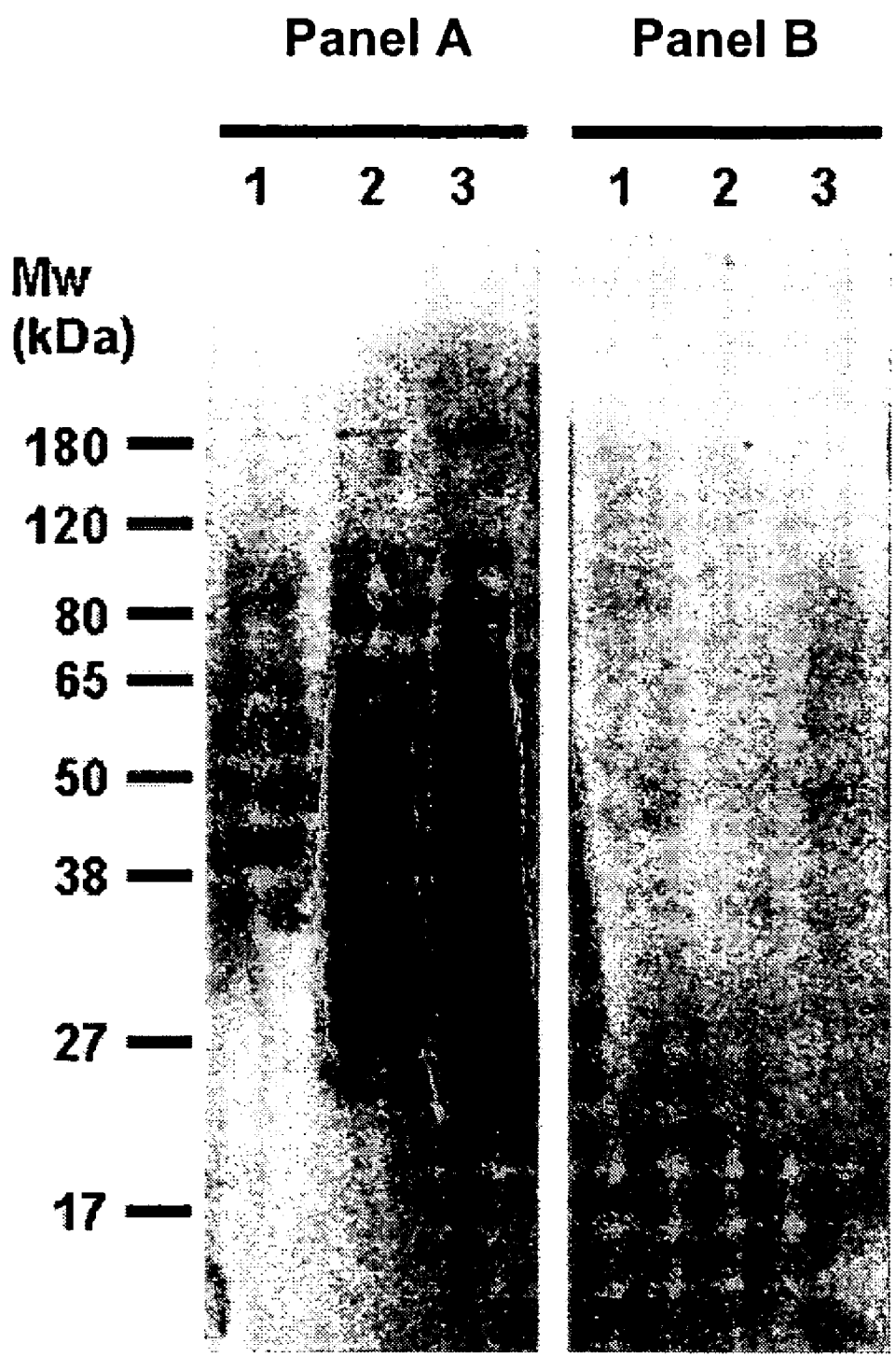
FIG. 1. Western blot of MDA-MB-231 whole cell lysates (Lane 1) or membranes (Lanes 2 and 3) probed with 7BD-33-11A (Panel A) or isotype control (Panel B). Molecular weight markers are indicated on the left.

Identification of Binding Proteins by Western Immunoblotting

To identify the antigen(s) recognized by the antibody 7BD-33-11A, cell membrane preparations were subjected to sodium dodecylsulphate polyacrylamide gel electrophoresis (SDS-PAGE), and transferred to membranes. The latter were probed with the antibody 7BD-33-11A to visualize the proteins detected by this antibody.

1 Whole Cell Lysate and Total Membrane Fraction Preparation 1.1. Whole Cell Lysate Preparation Previous work by FACS demonstrated binding of antibody 7BD-33-11A to the breast cancer cell line MDA-MB-231 (MB-231). As a result total cell membrane preparations and whole cell lysates obtained from this cell line were used for the antigen identification and characterization. Total cell lysate from MB-231 cells was prepared as follows: MB-231 cell pellet (1.5 g) was resuspended in 2 mL lysis buffer containing 20 mM Tris, pH 7.4, 150 mM NaCl, 1% (v/v) Triton X-100, 0.02% (w/v) sodium azide, 2 mM sodium orthovanadate, 50 mM sodium fluoride, and a protease inhibitor cocktail (Roche Diagnostics; Manheim, Germany). The pellet was homogenized with a glass homogenizer and was incubated with stirring, for 1 hr at 4° C. Samples were then subjected to centrifugation (20,000 g) for 15 min at 4° C., to remove detergent insoluble material. Supernatants were collected, divided in aliquots, and frozen at −80° C. The protein concentration in the cell lysate was determined by the BCA (bicinchoninic acid) assay (Pierce; Rockford, Ill.).

1.2. Total Cell Membrane Fraction Preparation

Total cell membranes were prepared from confluent cultures of MB-231 breast cancer cells. Media was removed from cell stacks and the cells were washed with phosphate buffered saline (PBS). Cells were dissociated with dissociation buffer (Gibco-BRL; Grand Island, N.Y.) for 20 min at 37° C. on a platform shaker. Cells were collected and centrifuged at 900 g for 10 min at 4° C. After centrifugation, cell pellets were washed by resuspending in PBS and centrifuging again at 900 g for 10 min at 4° C. Pellets were then stored at −80° C. until required. To prepare membranes, cell pellets were thawed and resuspended in homogenization buffer containing 1 tablet per 50 mL of complete protease inhibitor cocktail (Roche; Laval QC) at a ratio of 3 mL buffer per gram of cells. The cell suspension was subjected to homogenization using a polytron homogenizer on ice in order to lyse the cells. The cell homogenate was centrifuged at 15,000 g for 10 min at 4° C. to remove the nuclear particulate. Supernatant was harvested, divided into tubes and then centrifuged at 75,600 g for 90 min at 4° C. Supernatant was carefully removed and each membrane pellet was resuspended in approximately 5 mL of homogenization buffer. The membrane pellets from all tubes were combined, divided one more time, and centrifuged at 75,600 g for 90 min at 4° C. Supernatant was carefully removed and the pellets were weighed. Solubilization buffer containing 1% Triton X-100 was added to the pellets at a ratio of 3 mL buffer per gram of membrane pellet. Membranes were solubilized by shaking on a platform shaker at 300 rpm, for 1 hr on ice. The membrane suspension was centrifuged at 75,600 g to pellet insoluble material. The supernatant, containing the solubilized membrane proteins, was carefully removed from the tubes, assayed for protein concentration, and stored at −80° C.

2.1-Dimensional SDS-PAGE and Western Immunoblotting

Figure 2:
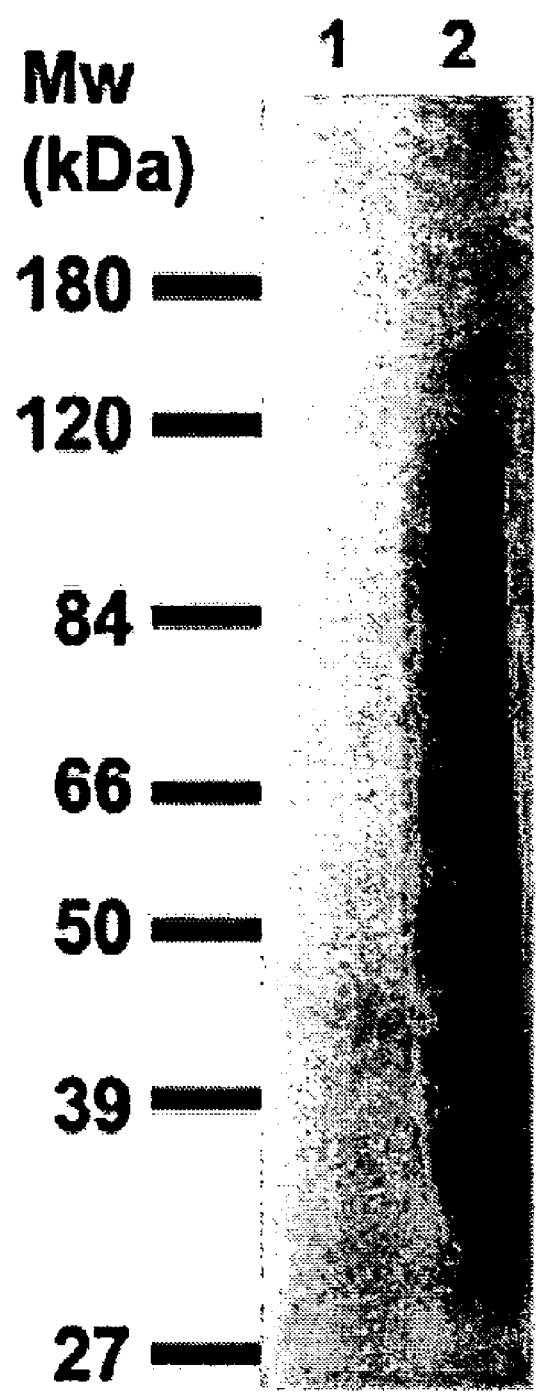
FIG. 2. Western blot of MDA-MB-231 membranes probed with 7BD-33-11A. Lane 1: Membrane run under reducing conditions. Lane 2: Membranes run under non-reducing conditions. Molecular weight markers are indicated on the left.

Proteins from the total membrane fraction and whole cell lysate of MB-231 cells were separated by 1-dimensional SDS-PAGE (1D. SDS-PAGE), on a 5 and 10 percent stacking and separating gel, respectively. Proteins were transferred overnight, at 4° C., by electroblotting onto PVDF membranes (Millipore; Billerica, Mass.). Complete transfer was determined by assessing the transfer of prestained molecular weight markers onto the membrane. After transfer, the membranes were blocked with 5 percent (w/v) skim milk in TBST, for 1 hr at room temperature (RT), and two replicate blots were then probed as follows: one blot was probed with the antibody 7BD-33-11A (5 µg/ml, in 5 percent skim milk in TBST) and the replicate blot was probed with an $IgG_{2a}$ isotype control (5 µg/ml, in 5 percent skim milk in TBST). Blots were washed 3 times for 10 min in TBST and then incubated with horseradish HRP-conjugated goat anti-mouse IgG (Fc) (Bio-Rad Laboratories; Hercules, Calif.), for 1 hr at RT. After washing 3 times for 10 min each with TBST, the blots were developed with the TMB peroxidase substrate kit (Vector Laboratories; Burlingame, Calif.) following the manufacturers' instructions. The blots were rinsed with water and images were acquired with a gel documentation system (FIGS. 1 and 2) (Bio-Rad; Hercules, Calif.). Blots were imaged under the same conditions of camera focus, aperture and image acquisition time. In FIG. 1, 7BD-33-11A clearly bound to proteins in the 20-80 kDa range, and its reactivity was detected in the lanes containing whole cell lysate and total membrane fraction. The isotype control did not bind to any proteins in the MB-231 lysate or membrane fractions, indicating that the binding for 7BD-33-11A was specific. FIG. 2 demonstrated the effect of sample reduction on 7BD-33-11A binding, on a Western blot. Reactivity of this antibody was only detected when the samples were prepared under non-reducing conditions (Lane 2). Reducing agents such as DTT or β-mercaptoethanol completely eliminated binding (Lane 1), indicating that recognition and binding of 7BD-33-11A to its epitope on the native protein depended on the presence of disulfide bonds.

Figure 3:
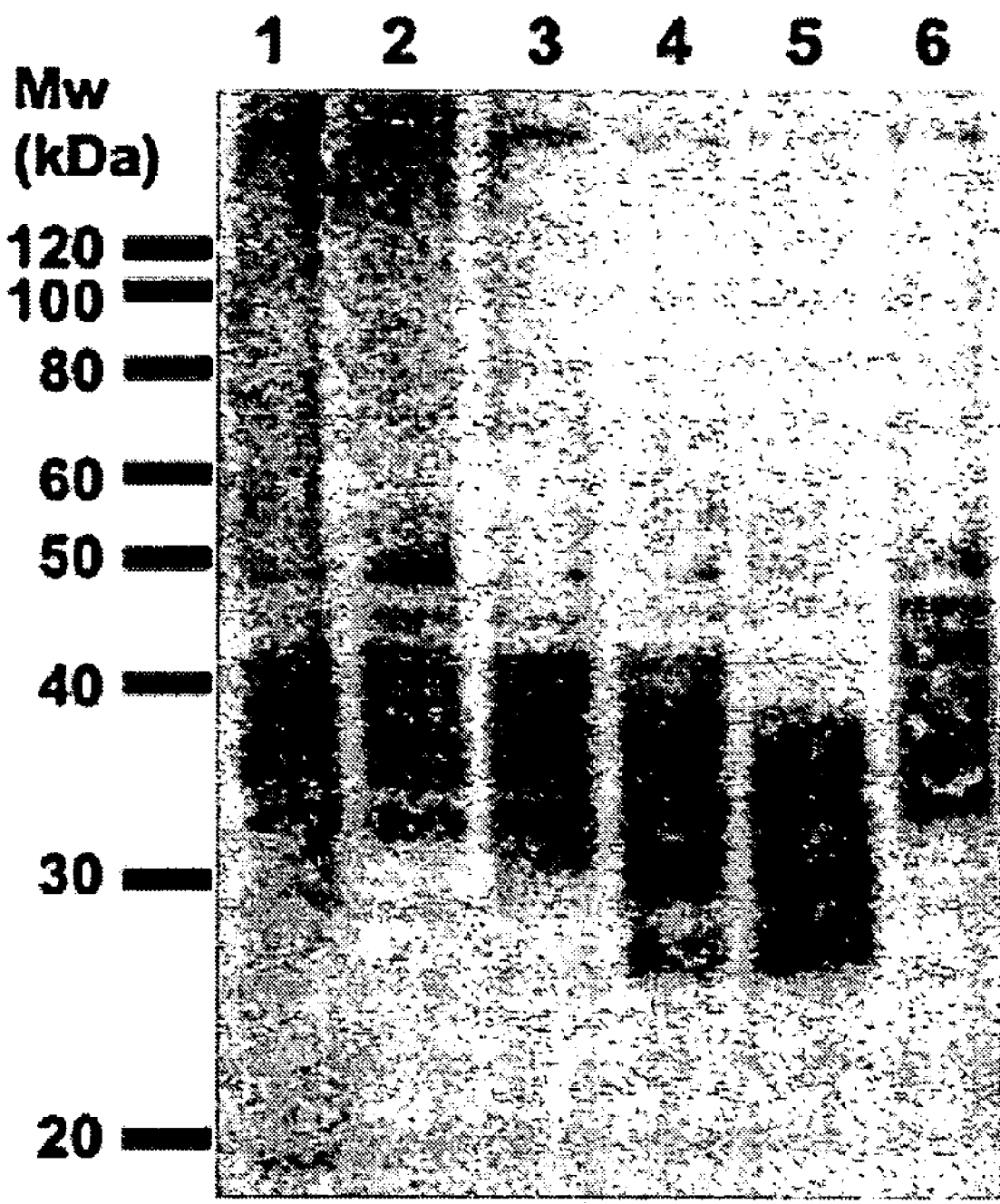
FIG. 3. Effect of deglycosylation on the binding of 7BD-33-11A to MDA-MB-231 membranes. MDA-MB-231 membranes were subjected to treatment with glycopeptidast F (PNGase F; Lane 1), O-glycanase (Lane 2), sialidase (Lane 3), the combination of PNGase F, O-glycanase and sialidase (Lane 4), the combination of PNGase F, O-glycanase, sialidase, galactosidase and glucosaminidase (Lane 5) or buffer control (Lane 6). Molecular weight markers are indicated on the left.

To determine if the disperse nature of the antigen, as detected by Western immunoblotting, was due to heterogeneous glycosylation, total membrane fractions were subjected to treatment with several glycosidases (glycopeptidase F, o-glycanase, sialidase, galactosidase and glucosaminidase) which removed specific carbohydrate groups. After treatment the samples were subjected to 1D SDS-PAGE and Western blotting. It was expected that if some of the enzymes removed a portion of carbohydrate that accounted for a significant amount of the mass of the antigen(s) recognized by the antibody 7BD-33-11A, that it would be possible to detect that difference by SDS-PAGE. FIG. 3 shows that glycosidase treatment of total membrane fractions from MB-231 cells resulted in a significant decrease in the mass of the recognized antigen(s). This indicated that the antigen recognized by the 7BD-33-11A antibody was comprised of at least one glycoprotein. The fact that a significant shift in the mobility of the antigen(s) only occurred when several enzymes were used together indicated that at least some of the carbohydrate moiety consisted of a complex N-linked carbohydrate. Although treatment of the membrane with glycosidases resulted in a molecular weight shift, it did not reduce the intensity of binding. This suggested that the antibody bound primarily to the polypeptide portion of the glycoprotein.

EXAMPLE 2

Identification of Antigens Bound by 7BD-33-11A

1. Immunoprecipitation of Antigens from MB-231 Total Membrane Fraction

Total membrane extracts (5 mg total protein) were diluted to a 1 mg/ml final protein concentration with the appropriate volume of 1× lysis buffer (50 mM Tris pH 7.4, 150 mM NaCl, 1% Triton X-100, 0.02% $NaN_3$, 2 mM sodium orthovanadate, 50 mM sodium fluoride, and protease inhibitor cocktail (Roche Diagnostics, Manheim, Germany)), and with the appropriate volume of 2× RIPA buffer (50 mM Tris pH 7.4, 150 mM NaCl, 1.0% sodium cholate, 0.2% SDS, 1% Triton X-100 and 0.02% $NaN_3$), in order to obtain a final 1× RIPA buffer concentration. The extracts were pre-cleared for 2 hr with protein G-Sepharose beads (Amersham Biosciences, Uppsala, Sweden) at 4° C. Total membrane extracts were removed and stock BSA (10 mg/ml) was added to a 0.5 mg/ml final BSA concentration. While extracts were being pre-cleared, antibody-conjugated protein G-Sepharose beads (60 µg of antibody chemically cross-linked to 30 µl of protein G Sepharose) were blocked with 1 mL of 0.5 mg/ml BSA, by incubation at 4° C., also for 2 hr. After blocking, the antibody-conjugated beads were washed twice for 5 min with 1× RIPA buffer. The antibody-conjugated protein G-Sepharose beads were then added to the BSA-containing total membrane extracts, and incubated for 3 hr, at 4° C., on an end-over-end rotator. After centrifugation at 20,000 g, for 10 seconds, at 4° C., the unbound fraction was removed and discarded, and the beads were washed 3 times for 5 min, with 1 mL of RIPA buffer in each wash step. The beads were then rinsed once with 1.5 ml of PBS. The immunoprecipitation (IP) described above, with 7

Figure 4:
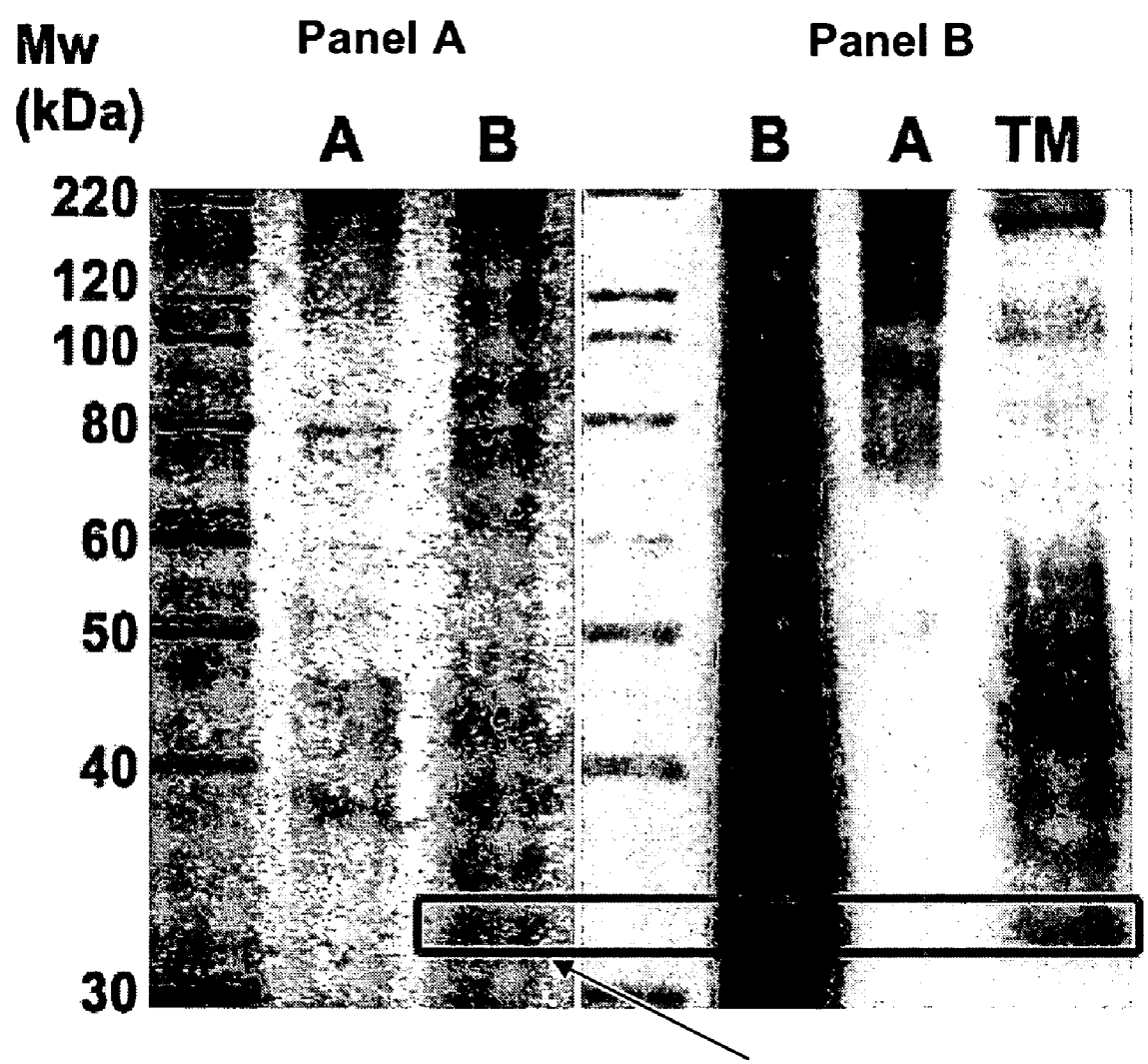
FIG. 4. SDS-PAGE (Panel A) and Western blot (Panel B) of MDA-MB-231 membrane proteins immunoprecipitated with 7BD-33-11A. Lane A isotype control immunoprecipitated proteins, Lane B: 7BD-33-11A immunoprecipitated proteins and Lane TM: Total MDA-MB-231 membrane proteins. Rectangular box outlines the same band from Lane B in the SDS-PAGE and Lane TM in the Western blot. Molecular weight markers are indicated on the left.

BD-33-11A-conjugated protein G Sepharose was carried out in parallel with a similar IP in which the protein G-Sepharose beads were chemically cross-linked with an $IgG_{2a}$ isotype control (BD Biosciences, San Diego, Calif.). This step was carried out to enable assessment of non-specific binding of proteins to the immunocomplexes. After completely draining the PBS, the beads were boiled in 40 μl of non-reducing sample buffer and the samples were analyzed by 1D SDS-PAGE followed by Western immunoblotting of a portion of the gel, and staining with Coomassie Colloidal Blue of the remaining portion of the gel. Of the 40 μl, a fraction (8 μl) was loaded onto the SDS-PAGE for Western blotting and the remaining fraction (32 μl) was loaded onto a separate lane of the same gel for protein staining with Coomassie Colloidal Blue. The portion of the gel designated for protein staining was incubated overnight with the Coomassie Colloidal Blue stain. The portion of the gel designated for Western blotting was transferred onto a PVDF membrane for 2 hr at 320 mA, rinsed with deionized water, blocked for 1 hr at RT with 5 percent milk in TBST and then incubated overnight at 4° C. with 7BD-33-11A in 5 percent milk in TBST. Blots were washed 3 times for 10 min in TBST and incubated with an HRP-conjugated Fc-specific goat anti-mouse IgG (1:5000) in 5 percent milk in TBST, for 1 hr at room temperature. Blots were then washed 3 times for 10 min and were developed according to the standard procedure of TMB substrate for HRP. As displayed in FIG. 4, the Western immunoblot and the Coomassie Colloidal Blue stained gel were lined up, using the molecular weight markers as reference. The main band that stained with Coomassie Colloidal Blue lined up with the main band that reacted with 7BD-33-11A on the Western blot. This section is highlighted (rectangle inset) on FIG. 4.

2. Peptide Mapping, and Antigen Identification by Mass Spectrometry

Figure 6:
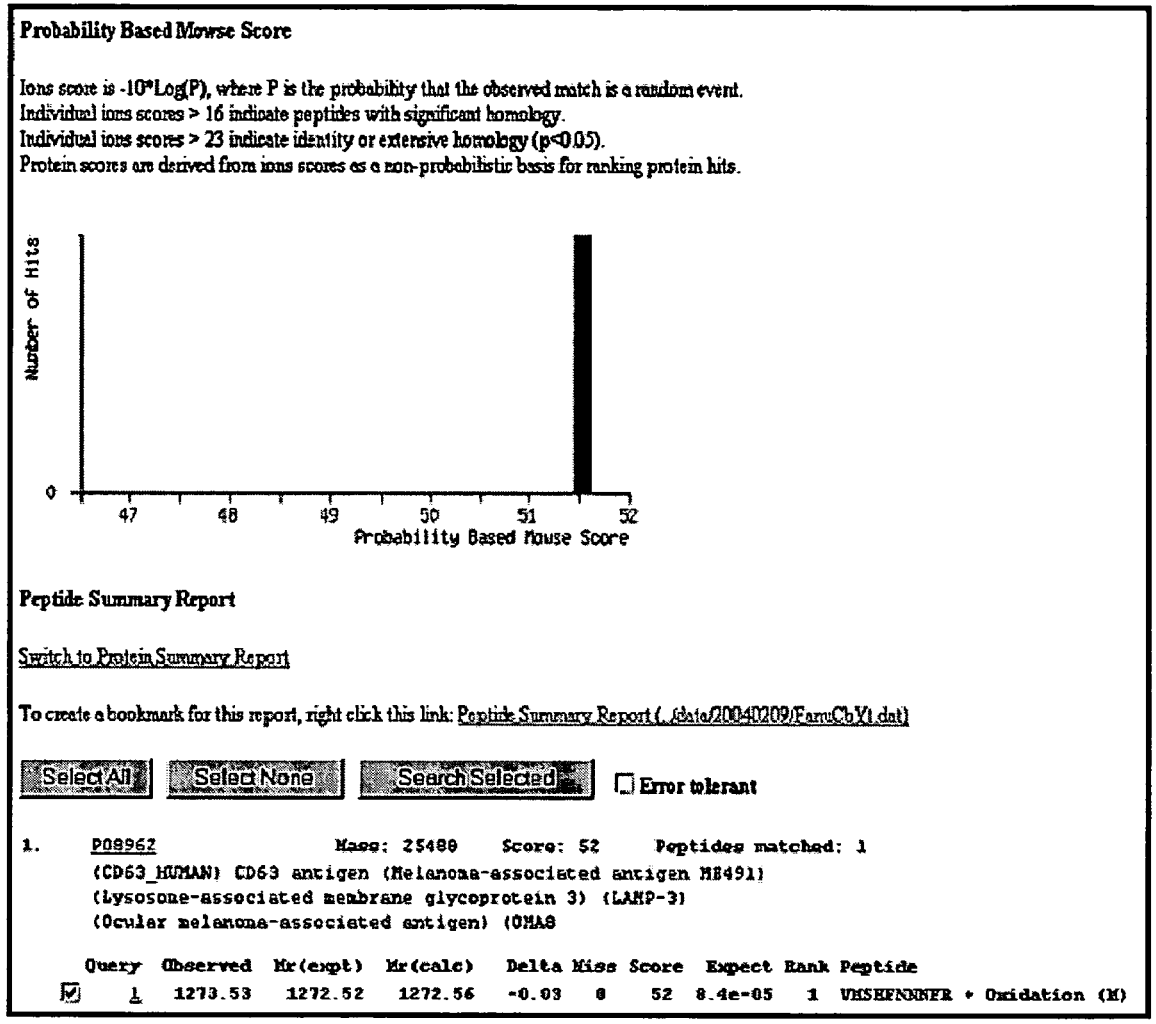
FIG. 6. MASCOT search summary table. The peptide disclosed in the lower right corner is designated SEQ ID NO:5.

From the experiment above, the band on the Coomassie Colloidal Blue stained gel that lined up with the most intense reactivity on the Western blot was then cut out and subjected to in-gel tryptic digestion using a commercially available kit (Pierce, Rockford, Ill.). Aliquots of the digest were subjected to mass spectrometry analysis on a SELDI-TOF Ciphergen PBSIIc reader (Ciphergen Biosystems Inc., Freemont, Calif.). Briefly, an aliquot of the digest was manually spotted onto an H4 chip (Ciphergen Biosystems Inc., Freemont, Calif.). After drying, an aliquot of CHCA matrix (α-cyano 4-hydroxy cinnaminic acid; Ciphergen Biosystems Inc., Freemont, Calif.) was added onto the same spot on the chip and allowed to dry. The sample was then analyzed on the PBSIIc reader. Similar sized bands from parallel regions on isotype control lanes and blank gel region were processed side-by-side with the gel plug from the 7BD-33-11A IP, so as to enable determination of unique peptide fragments generated by the digestion of the antigen immunoprecipitated by 7BD-33-11A. The masses of the unique peptide fragments were searched using PROFOUND, a publicly accessible online tool for searching protein sequence databases using information from mass spectra. The unique peptides in the sample from the 7BD-33-11A IP digest were then subjected to MS/MS analysis on a QSTAR (Applied Biosystems, Foster City, Calif.) equipped with an interface that enabled analysis of the same sample spots that were previously analyzed on the PBSIIc reader. The MS/MS data was then analyzed with MASCOT, a publicly accessible online tool for searching protein databases using information from MS/MS spectra. FIG. 5 is a summary of the table that resulted from the ProFound search. The only protein that was suggested as a putative candidate, with a significant degree of confidence was CD63. FIG. 6 is a summary table that resulted from the MASCOT search. The only protein that was identified with a high degree of probability was CD63, supporting the previous tentative identification by peptide map fingerprinting.

3. 7BD-33-11A Antigen ID Confirmation

Figure 7A:
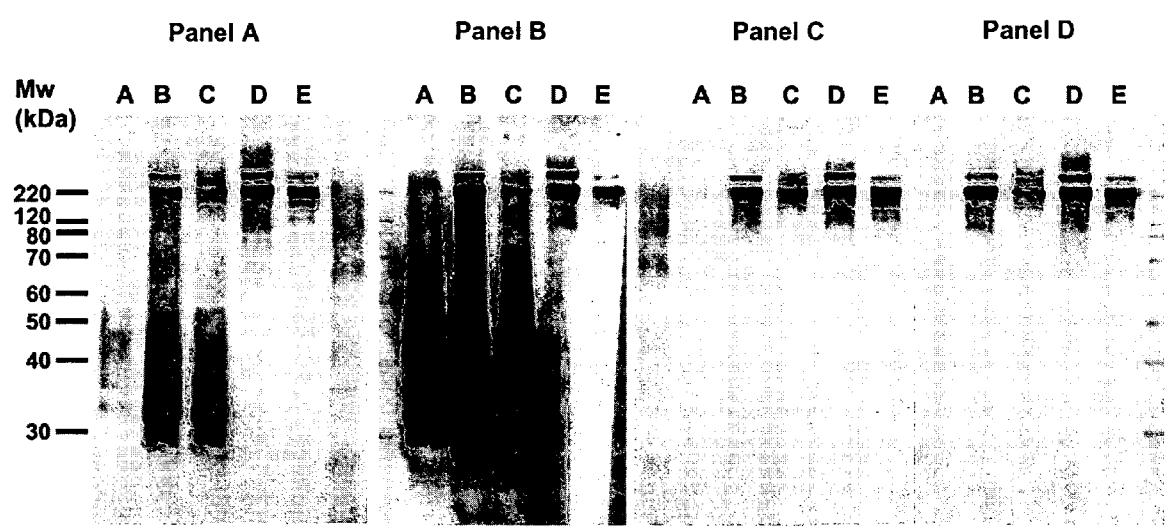
FIG. 7a: Western blots of proteins probed with 7BD-33-11A (Panel A), anti-CD63 (clone RFAC4, Panel B), IgG2a isotype control (Panel C) and IgG1 isotype control (Panel D). Lane A: Total MDA-MB-231 membrane proteins; Lane B: 7BD-33-11A immunoprecipitated proteins; Lane C: anti-CD63 (RFAC4) immunoprecipitated proteins, Lane D: IgG2a isotype control immunoprecipitated proteins and Lane E: IgG1 isotype control immunoprecipitated proteins. Molecular weight markers are indicated on the left.
Figure 7B:
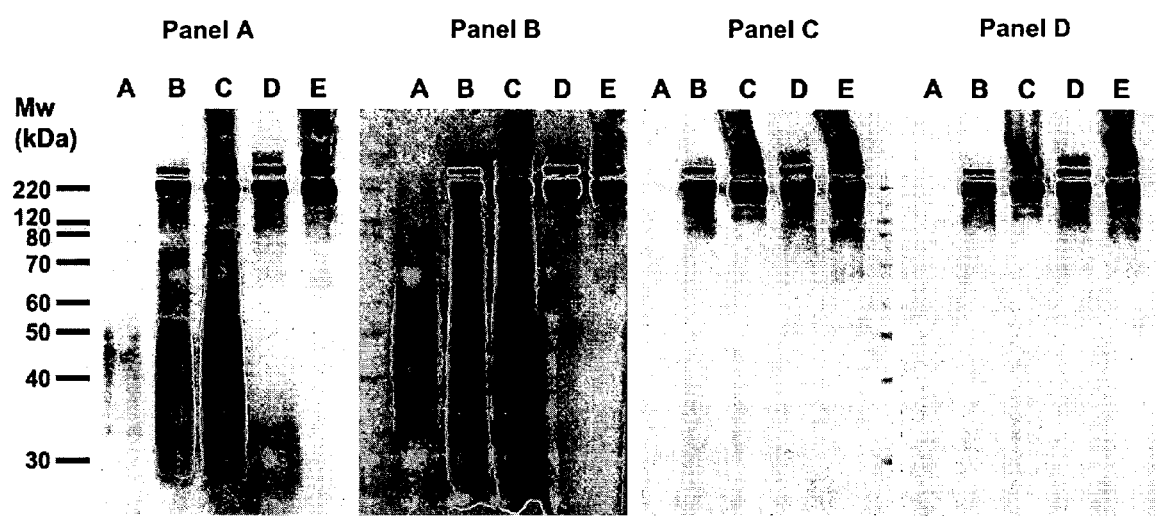
FIG. 7b: Western blots of proteins probed with 7BD-33-11A (Panel A), anti-CD63 (clone H5C6, Panel B), IgG2a isotype control (Panel C) and IgG1 isotype control (Panel D). Lane A: Total MDA-MB-231 membrane proteins; Lane B: 7BD-33-11A immunoprecipitated proteins; Lane C: anti-CD63 (H5C6) immunoprecipitated proteins, Lane D: IgG2a isotype control immunoprecipitated proteins and Lane E: IgG1 isotype control immunoprecipitated proteins. Molecular weight markers are indicated on the left.

Confirmation of the ID of the putative antigen for 7BD-33-11A was carried out through determination of whether known anti-human CD63 monoclonal antibodies (e.g. RFAC4 and H5C6) would react with the protein(s) immunoprecipitated by 7BD-33-11A, and vice versa. Further confirmation was also carried out by Western immunoblotting of total lysates from induced and non-induced bacteria transformed with glutathione S-transferase (GST)-fusion constructs of the extracellular domains of human CD63. Immunoprecipitates from MB-231 total membrane, and prepared with the monoclonal antibodies 7BD-33-11A, RFAC4 (Cymbus Biotechnology LTD, Hants, UK), H5C6 (BD Biosciences, San Diego, Calif.), and with the $IgG_{2a}$ and $IgG_1$(BD Biosciences, San Diego, Calif.) isotype controls, were analyzed by 1D SDS-PAGE followed by Western immunoblotting. Equal fraction volumes from each immunocomplex sample were analyzed on replicate gels. After electroblotting onto PVDF membranes, the blots from the replicate gels were probed in parallel with the monoclonal antibodies 7BD-33-11A, RFAC4, H5C6, and with the $IgG_{2a}$ and $IgG_1$ isotype controls. In FIG. 7a the result from the cross-IP experiments in which the material immunoprecipitated by each of the test monoclonal antibodies 7BD-33-11A and RFAC4 was analyzed by Western immunoblotting. In FIG. 7b the result from the cross-IP experiments in which the material immunoprecipitated by each of the test monoclonal antibodies 7BD-33-11A and H5C6 was analyzed by Western immunoblotting. Each of the monoclonal antibodies 7BD-33-11A, RFAC4 and H5C5 cross-reacted with similar antigen(s) immunoprecipitated by 7BD-33-11A. In addition, 7BD-33-11A cross reacted, on a Western blot, with similar antigen(s) immunoprecipitated by RFAC4 and H5C6, in the range of 20-80 kDa, but not with the immunocomplexes prepared with the isotype control antibodies. The blots probed with the isotype control antibodies were completely negative. This data indicated that the epitope recognized by the 7BD-33-11A antibody was contained within the CD63 antigen.

Figure 8:
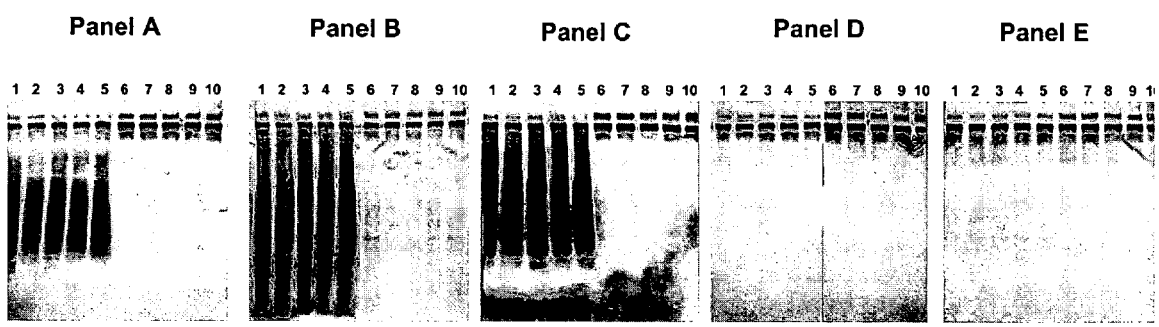
FIG. 8. Western blots of proteins probed with 7BD-33-11A (Panel A), anti-CD63 (clone RFAC4, Panel B), anti-CD63 (clone H5C6, Panel C), IgG2a isotype control (Panel D) and IgG1 isotype control (Panel E). Lanes 1-5 contain 7BD-33-11A immunoprecipitated proteins and Lanes 6-10 contain IgG2a isotype control immunoprecipitated proteins. Lanes 1 and 6: no NaCl, Lanes 2 and 7: 150 mM NaCl, Lanes 3 and 8: 500 mM NaCl, Lanes 4 and 9: 2000 mM NaCl and Lanes 5 and 10: RIPA buffer.

To determine if the cross-reactivity could be due to the same molecules being recognized by all antibodies, or if it was due to the presence of interacting molecules with similar mass, immunoprecipitations with the antibody 7BD-33-11A were carried out in conditions of increasing buffer stringency (50 mM Tris pH 7.4, 1% Triton X-100, and varying concentrations of NaCl: 0, 150, 500 and 2000 mM; and also with RIPA buffer as described above but containing 500 mM NaCl). The resulting immunocomplexes were then probed by Western immunoblotting with the monoclonal antibodies 7BD-33-11A, H5C6 and RFAC4 and with the isotype controls $IgG_{2a}$ and $IgG_1$. FIG. 8 showed that varying the stringency of the IP conditions did not have any detectable impact on the formation of the immunocomplexes, which indicated that the molecule(s) recognized by the antibody 7BD-33-11A were also recognized by the anti-CD63 antibodies and vice versa.

To further confirm that 7BD-33-11A was directly binding to the human CD63 antigen, its reactivity was assessed, by Western immunoblotting against lysates of *E. coli* expressing recombinant fusion polypeptides containing the extracellular domains (loops EC1 and EC2) of human CD63. For this work, GST-fusion constructs of the extracellular loops of CD63 (loop 1 and loop 2-EC1 and EC2, respectively) were generated by subcloning the appropriate cDNA fragments into the bacterial expression vector PGEX-4T-2 (Amersham Biosciences, Piscataway, N.J.). The cDNA fragments encoding the loops were obtained by polymerase chain reaction amplification (PCR), using the full-length human cDNA as a template (clone MGC-8339, American Type Culture Collection Manassas, Va.). The cDNA encoding the EC1 loop was obtained using the following PCR primers: 5' primer (EC1_5'), 5'GCCGTGGGATCCGGGGCACAGCTTGTCCTG3' (SEQ ID NO:1) and 3' primer (EC1_3'), 5'GATGACGAATTCTCACAGAGAGCCAGGGGTAGC3' (SEQ ID NO:2). The cDNA encoding the EC2 loop was obtained using the following PCR primers: 5' primer (EC2_5'), 5'GGCTATGGATCCAGAGATAAGGGTGATG3' (SEQ ID NO:3) and 3' primer (EC2_3'), 5'TACCAGAATTCAATTTTTCCTCAGCCAGCC3' (SEQ ID NO:4). The conditions for the PCR reactions were as follows: 2 µL of 5' primer (25 pmol/µL), 2 µL of 3' primer (25 pmol/µL), 0.2 µL of template DNA (pOTB-CD63, 0.76 mg/mL), and 45.8 µL of PCR SuperMix High Fidelity (Invitrogen, Burlington, ON). The PCR reaction was carried out as follows: 94° C. for 5 min followed by 30 cycles of: melting at 94° C. for 30 sec, annealing at 55° C. for 30 sec and extension at 72° C. for 1 min, per cycle.

After subcloning, the constructs, including a PGEX-4T-2 vector alone negative control (no cDNA fragment subcloned into the vector), were transformed into *E. coli* (strain BL-21). A single ampicillin-resistant colony from each transformation was grown and the respective insert cDNAs were sequenced. After confirming that the cDNA sequence was correct, each of the clones was grown in liquid culture and the expression of the GST-fusion constructs was induced by addition of 1 mM IPTG (isopropyl-β-D-thiogalactopyranoside) (Gibco-BRL; Rockville, Md.). After a 2 hr incubation, the bacteria culture was centrifuged at 2000 g, for 5 min, at room temperature. The supernatant was discarded and the bacteria pellets were boiled in non-reducing SDS-PAGE sample buffer. The samples were then analyzed by SDS-PAGE (5 and 12 percent) polyacrylamide stacking and separating gels respectively) and Western immunoblotting, as previously described. Blot membranes were probed with 7BD-33-11A, H5C6, RFAC4, or with an IgG2a isotype control. The results illustrated by FIG. 9 revealed that 7BD-33-11A specifically recognized loop 2 (amino acids 108-202) of human CD63 (lane 6 of blot probed with 7BD-33-11A), and does not recognize loop 1 (amino acids 34-52). The specificity of the antibody against the bacterial lysate was further confirmed by the observation that two well-characterized anti-human CD63 antibodies (RFAC4 and H5C6) also recognized a similar size band, only on the lysates from induced *E. coli* expressing the EC2 fusion polypeptide. All of the above results demonstrate that 7BD-33-11A recognized and directly bound to human CD63, and specifically to the extracellular region encompassing amino acids 108-202.

EXAMPLE 3

As outlined in Ser. No. 10/348,231, the hybridoma cell line 7BD-33-11A was deposited, in accordance with the Budapest Treaty, with the American Type Culture Collection, 10801 University Blvd., Manassas, Va. 20110-2209 on Jan. 8, 2003, under Accession Number PTA-4890. In accordance with 37 CFR 1.808, the depositors assure that all restrictions imposed on the availability to the public of the deposited materials will be irrevocably removed upon the granting of a patent.

Antibody Production:

7BD-33-11A monoclonal antibody was produced by culturing the hybridoma in CL-1000 flasks (BD Biosciences, Oakville, ON) with collections and reseeding occurring twice/week. The antibody was purified according to standard antibody purification procedures with Protein G Sepharose 4 Fast Flow (Amersham Biosciences, Baie d'Urfé, QC).

As previously described in Ser. No. 10/348,231, 7BD-33-11A was compared to a number of both positive (anti-Fas (EOS9.1, IgM, kappa, 20 micrograms/mL, eBioscience, San Diego, Calif.), anti-Her2/neu (IgG1, kappa, 10 microgram/mL, Inter Medico, Markham, ON), anti-EGFR (C225, IgG1, kappa, 5 microgram/mL, Cedarlane, Hornby, ON), Cycloheximide (100 micromolar, Sigma, Oakville, ON), $NaN_3$ (0.1%, Sigma, Oakville, ON)) and negative (107.3 (anti-TNP, IgG1, kappa, 20 microgram/mL, BD Biosciences, Oakville, ON), G155-178 (anti-TNP, IgG2a, kappa, 20 microgram/mL, BD Biosciences, Oakville, ON), MPC-11 (antigenic specificity unknown, IgG2b, kappa, 20 microgram/mL), J606 (anti-fructosan, IgG3, kappa, 20 microgram/mL), IgG Buffer (2%)) controls in a cytotoxicity assay (Table 2). Breast cancer (MDA-MB-231 (MB-231), MDA-MB-468 (MB-468), MCF-7), colon cancer (HT-29, SW1116, SW620), lung cancer (NCI H460), ovarian cancer (OVCAR), prostate cancer (PC-3), and non-cancer (CCD 27sk, Hs888 Lu) cell lines were tested (all from the ATCC, Manassas, Va.). The Live/Dead cytotoxicity assay was obtained from Molecular Probes (Eugene,Oreg.). The assays were performed according to the manufacturer's instructions with the changes outlined below. Cells were plated before the assay at the predetermined appropriate density. After 2 days, purified antibody or controls were diluted into media, and then 100 microliters were transferred to the cell plates and incubated in a 5 percent $CO_2$ incubator for 5 days. The plate was then emptied by inverting and blotted dry. Room temperature DPBS containing $MgCl_2$ and $CaCl_2$ was dispensed into each well from a multi-channel squeeze bottle, tapped three times, emptied by inversion and then blotted dry. 50 microliters of the fluorescent calcein dye diluted in DPBS containing $MgCl_2$ and $CaCl_2$ was added to each well and incubated at 37° C. in a 5 percent $CO_2$ incubator for 30 minutes. The plates were read in a Perkin-Elmer HTS7000 fluorescence plate reader and the data was analyzed in Microsoft Excel and the results were tabulated in Table 1. The data represented an average of four experiments tested in triplicate and presented qualitatively in the following fashion: 4/4 experiments greater than threshold cytotoxicity (+++), 3/4 experiments greater than threshold cytotoxicity (++), 2/4 experiments greater than threshold cytotoxicity (+). Unmarked cells in Table 1 represent inconsistent or effects less than the threshold cytotoxicity. The 7BD-33-11A antibody demonstrated cytotoxicity in a breast and prostate tumor cell line selectively, while having no effect on non-transformed normal cells. 7BD-33-11A demonstrated greater killing than the positive control anti-Fas antibody on the prostate cancer cell line. The chemical cytotoxic agents induced their expected cytotoxicity while a number of other antibodies which were included for comparison also performed as expected given the limitations of biological cell assays. In toto, it was shown that the 7BD-33-11A antibody has cytotoxic activity against a number of cancer cell types. The antibody was selective in its activity since not all cancer cell types were susceptible. Furthermore, the antibodies demonstrated functional specificity since they did not produce cytotoxicity against non-cancer cell types, which is an important factor in a therapeutic situation.

TABLE 1

| | | BREAST | | | COLON | | | LUNG | OVARY | PROSTATE | NORMAL | |
|---|---|---|---|---|---|---|---|---|---|---|---|---|
| | | MB-231 | MB-468 | MCF-7 | HT-29 | SW1116 | SW620 | NCI H460 | OVCAR | PC-3 | CCD 27 sk | Hs888 Lu |
| Positive Controls | 7BD-33-11A | − | − | + | − | − | − | − | − | ++ | − | − |
| | anti-Fas | − | − | +++ | − | − | − | − | +++ | + | − | + |
| | anti-Her2 | + | − | + | − | − | − | − | + | − | − | − |
| | anti-EGFR | − | +++ | + | − | +++ | − | − | + | − | + | − |
| | CHX (100 μM) | +++ | +++ | +++ | +++ | +++ | +++ | +++ | +++ | +++ | +++ | +++ |
| | NaN$_3$(0.1%) | +++ | +++ | +++ | +++ | − | − | +++ | +++ | +++ | − | − |
| Negative Controls | IgG1 | | | | | | | | +++ | + | | |
| | IgG2a | | | +++ | | + | | | | | | |
| | IgG2b | | | +++ | | | | | | | | |
| | IgG3 | | | | | | | | | | | |
| | IgG Buffer | + | | | | | | | | | | |

Binding of 7BD-33-11A to the above-mentioned panel of cancer and normal cell lines and to the following additional cancer cell lines; colon (LOVO), pancreatic (BxPC-3), ovarian (ES-2, OCC-1) and prostate (DU-145) and the following additional normal cell line (CCD-112) was assessed by flow cytometry (FACS). Cells were prepared for FACS by initially washing the cell monolayer with DPBS (without Ca$^{++}$ and Mg$^{++}$). Cell dissociation buffer (INVITROGEN, Burlington, ON) was then used to dislodge the cells from their cell culture plates at 37° C. After centrifugation and collection the cells were resuspended in Dulbecco's phosphate buffered saline containing MgCl$_2$, CaCl$_2$ and 2 or 25 percent fetal bovine serum (FBS) at 4° C. (wash media) and counted, aliquoted to appropriate cell density, spun down to pellet the cells and resuspended in staining media (DPBS containing MgCl$_2$ and CaCl$_2$ +/−2 percent FBS) containing 7BD-33-11A or control antibodies (isotype control or anti-EGFR) at 20 μg/mL on ice for 30 min. Prior to the addition of Alexa Fluor 488-conjugated secondary antibody the cells were washed once with wash media. The Alexa Fluor 488-conjugated antibody in staining media was then added for 20 to 30 min. The cells were then washed for the final time and resuspended in staining media containing 1 μg/mL propidium iodide or 1.5 percent paraformaldehyde. Flow cytometric acquisition of the cells was assessed by running samples on a FACScan using the CellQuest software (BD Biosciences). The forward (FSC) and side scatter (SSC) of the cells were set by adjusting the voltage and amplitude gains on the FSC and SSC detectors. The detectors for the three fluorescence channels (FL1, FL2, and FL3) were adjusted by running cells stained with purified isotype control antibody followed by Alexa Fluor 488-conjugated secondary antibody such that cells had a uniform peak with a median fluorescent intensity of approximately 1-5 units. Live cells were acquired by gating for FSC and propidium iodide exclusion (when used). For each sample, approximately 10,000 live cells were acquired for analysis and the resulted presented in Table 2. Table 2 tabulated the mean fluorescence intensity fold increase above isotype control and is presented qualitatively as: less than 5 (−); 5 to 50 (+); 50 to 100 (++); above 100 (+++) and in parenthesis, the percentage of cells stained.

Figure 9:
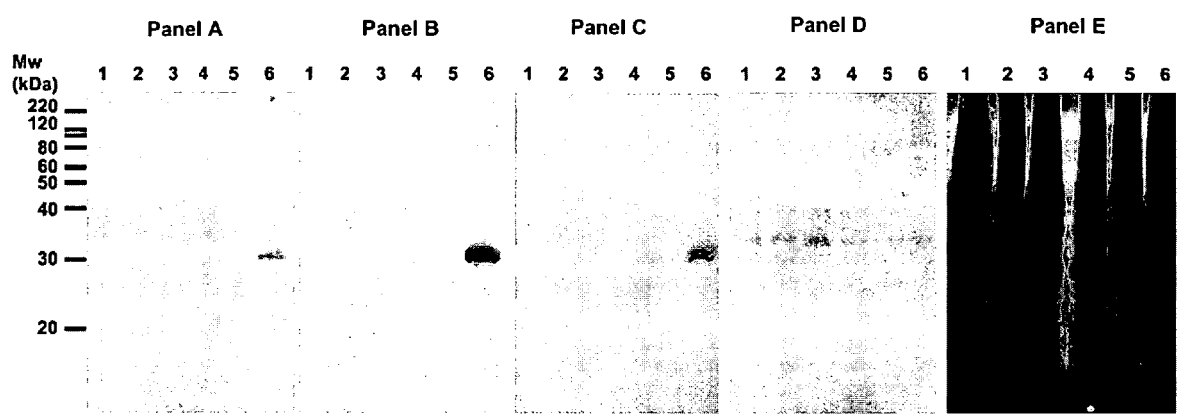
FIG. 9. Western blots of proteins probed with 7BD-33-11A (Panel A), anti-CD63 (clone RFAC4, Panel B), anti-CD63 (clone H5C6, Panel C), IgG2a isotype control (Panel D) and Coomassie Colloidal Blue protein stain (Panel E). Lane 1: non-induced vector alone, Lane 2: non-induced GST-EC1, Lane 3: non-induced GST-EC2, Lane 4: induced vector alone, Lane 5: induced GST-EC1 and Lane 6: induced GST-EC2. Molecular weight markers are indicated on the left.
Figure 10:
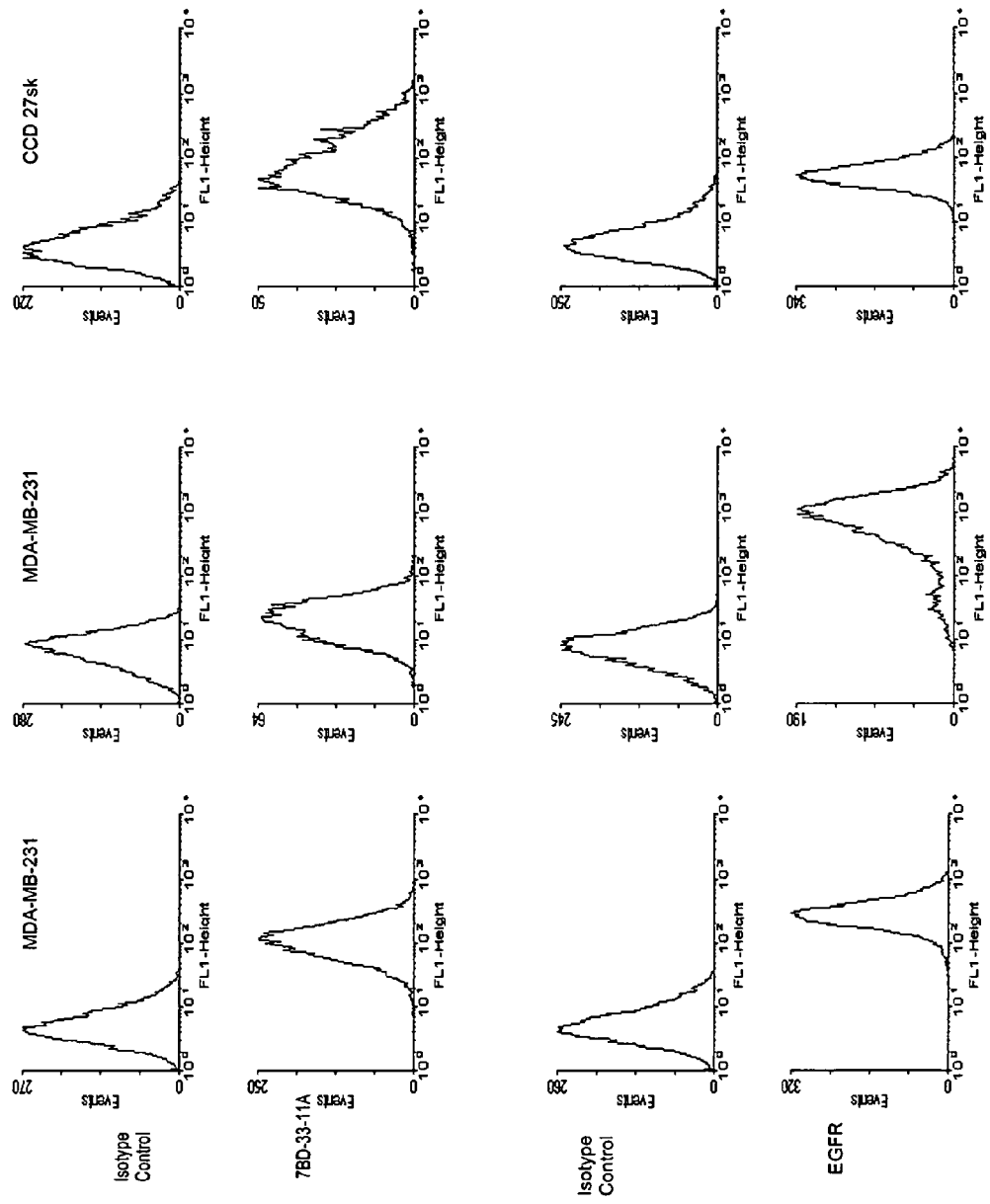
FIG. 10. Representative FACS histograms of 7BD-33-11A, isotype controls and anti-EGFR directed against several cancer cell lines and non-cancer cells.
Figure 15:
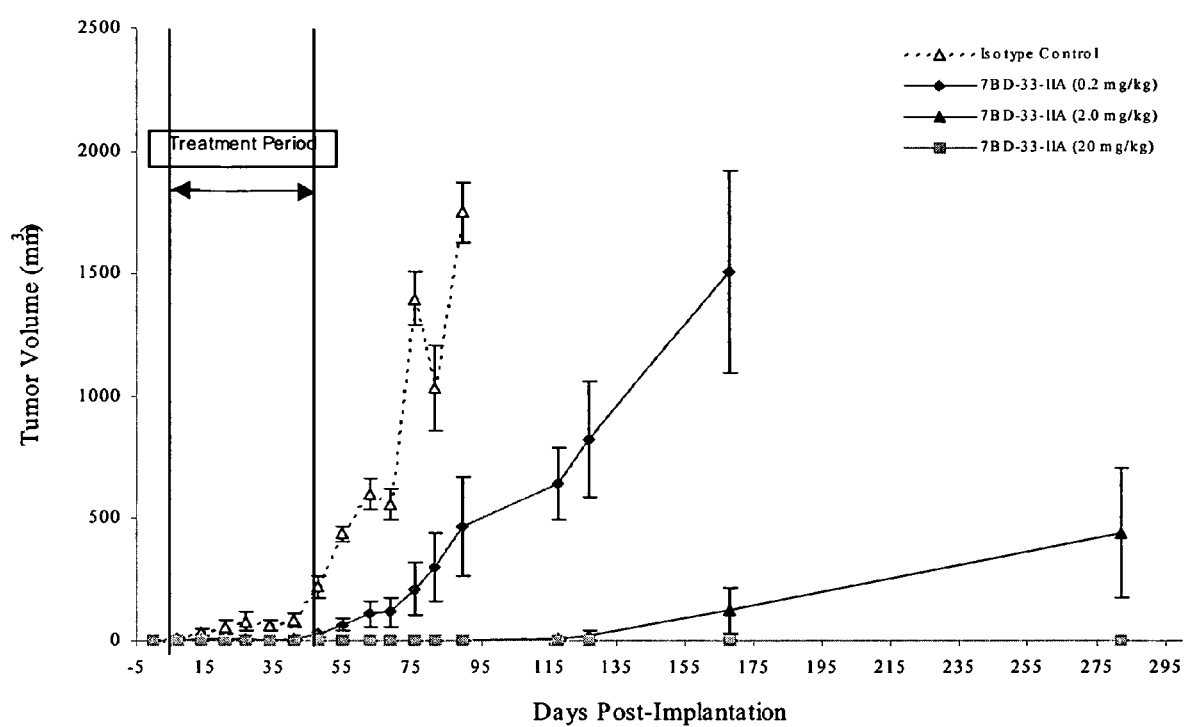
FIG. 15. Effect of 7BD-33-11A or isotype control on tumor growth in a dose response preventative MDA-MB-231 breast cancer model. The dashed line indicates the period during which the antibody was administered. Data points represent the mean +/−SEM.
Figure 16:
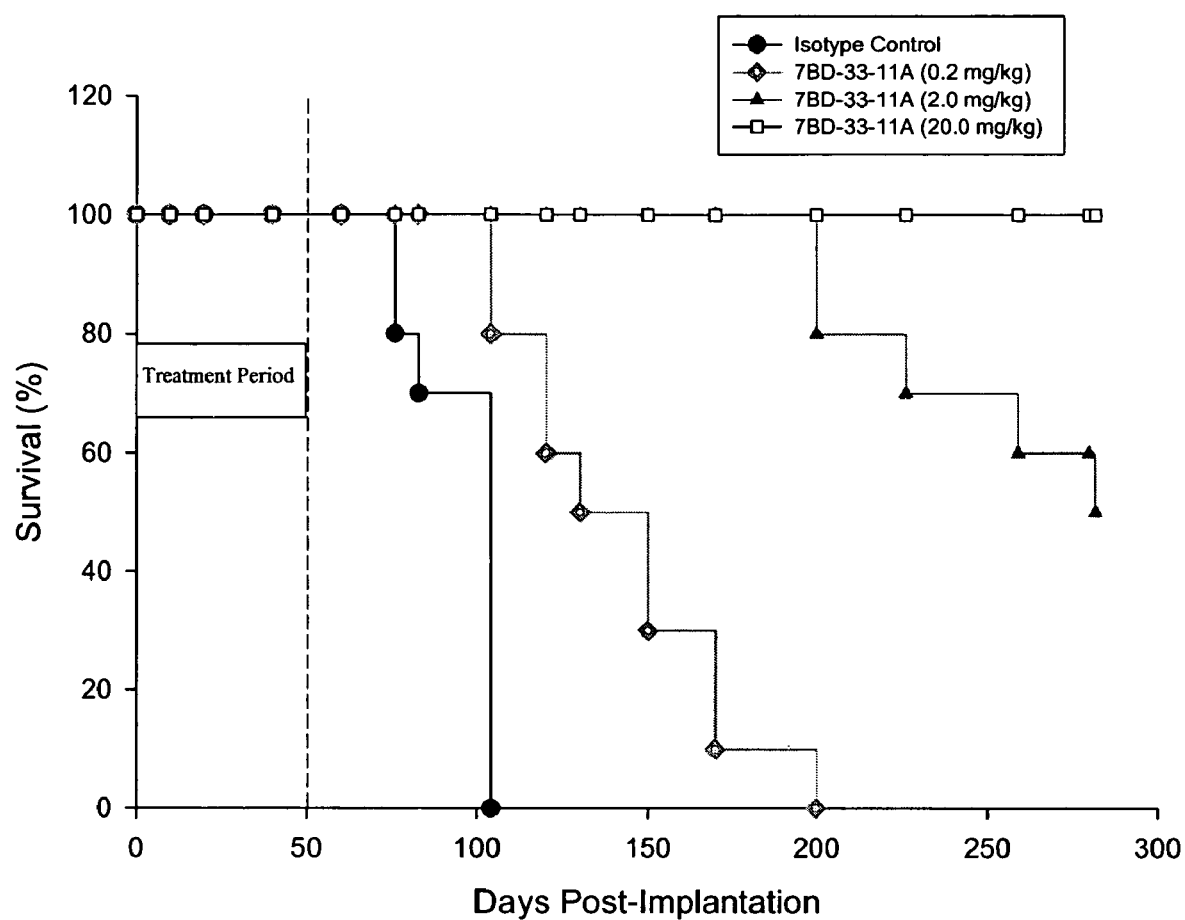
FIG. 16. Survival of tumor-bearing mice after treatment with 7BD-33-11A or isotype control antibody in a dose response preventative MDA-MB-231 xenograft study.
Figure 17:
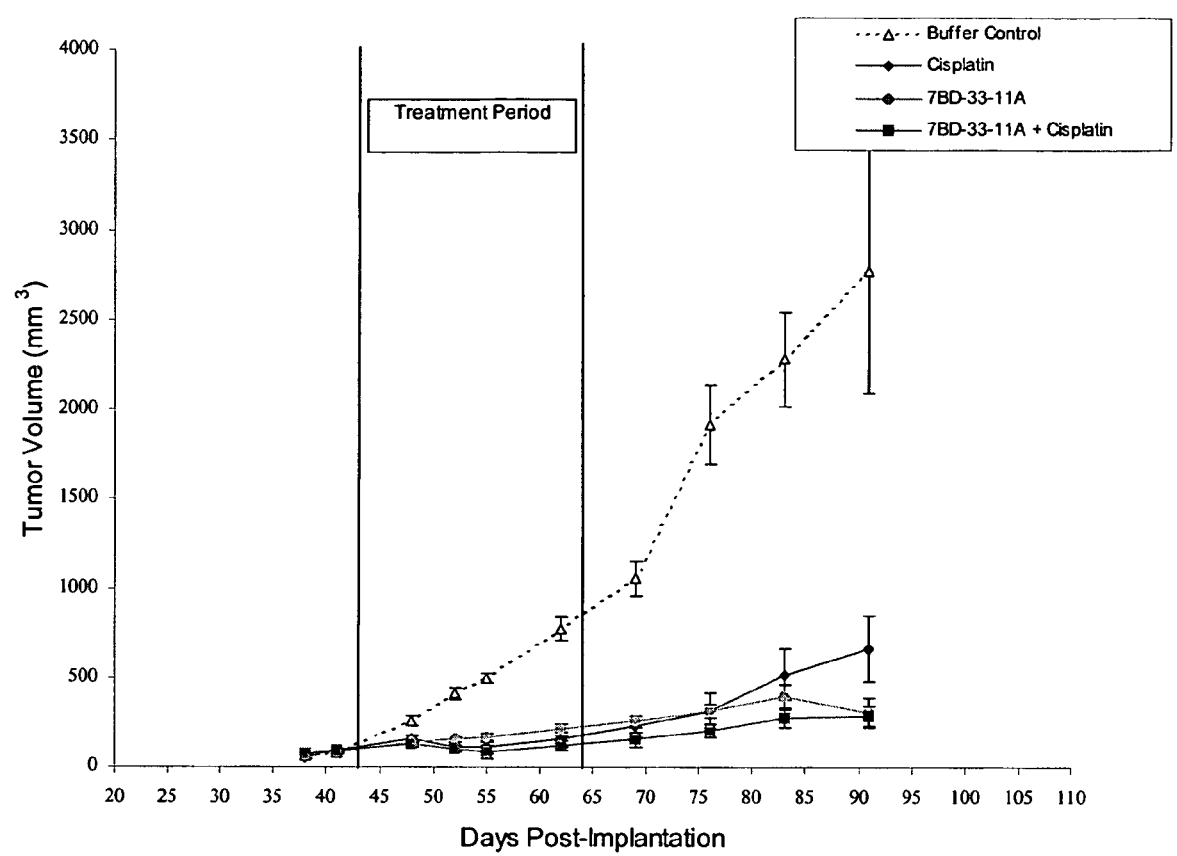
FIG. 17. Effect of 7BD-33-11A, Cisplatin, 7BD-33-11A+ Cisplatin or buffer control on tumor growth in an established MDA-MB-231 breast cancer model. The dashed line indicates the period during which the antibody was administered. Data points represent the mean +/−SEM.
Figure 18:
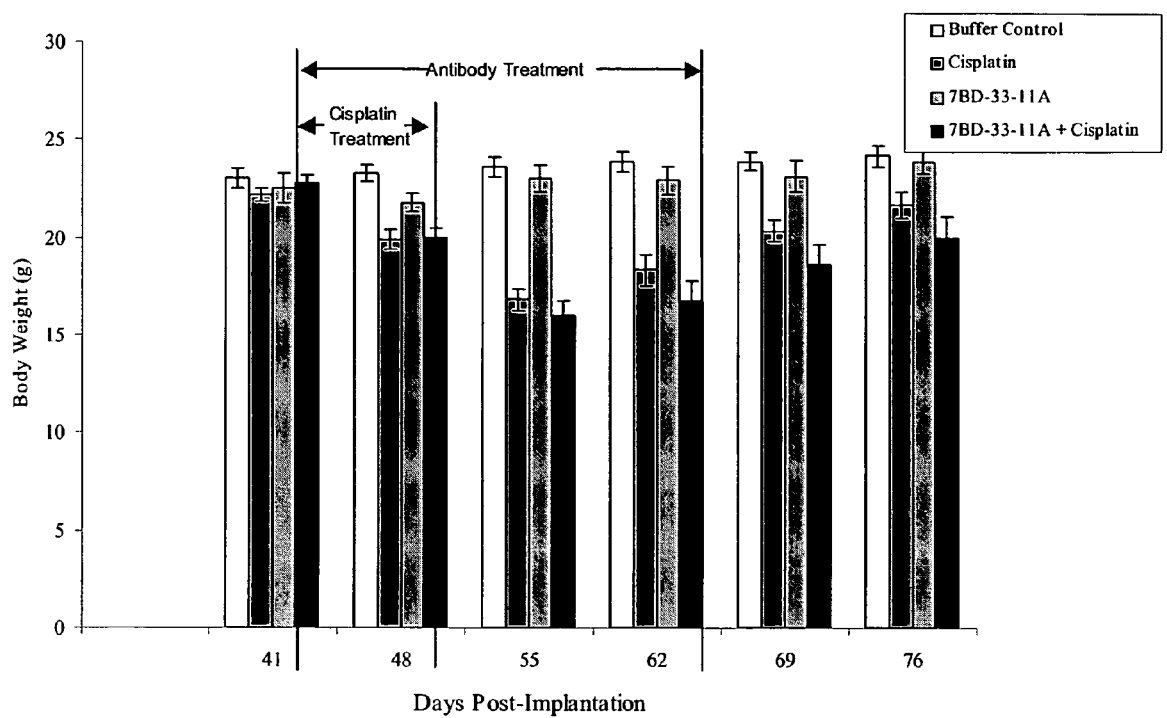
FIG. 18. Effect of 7BD-33-11A, Cisplatin, 7BD-33-11A+ Cisplatin or buffer control on body weight in an established MDA-MB-231 breast cancer model.
Figure 19:
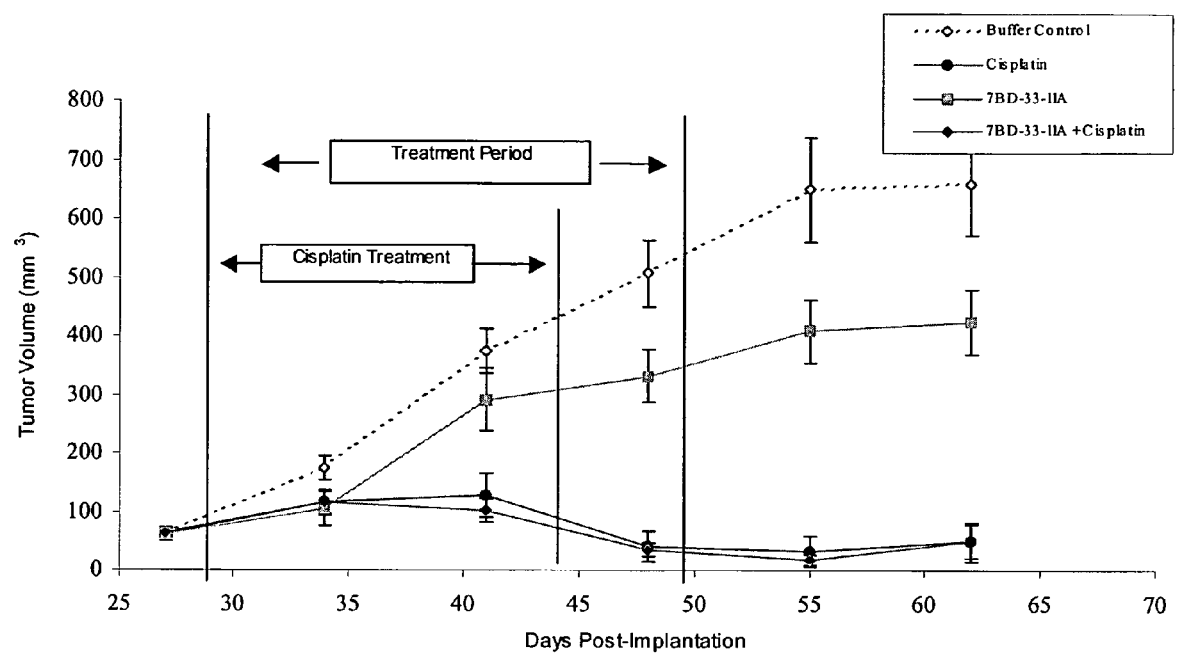
FIG. 19. Effect of 7BD-33-11A, Cisplatin, 7BD-33-11A+ Cisplatin or buffer control on tumor growth in an established MDA-MB-468 breast cancer model. The dashed line indicates the period during which the antibody/Cisplatin was administered. Data points represent the mean +/−SEM.
Figure 20:
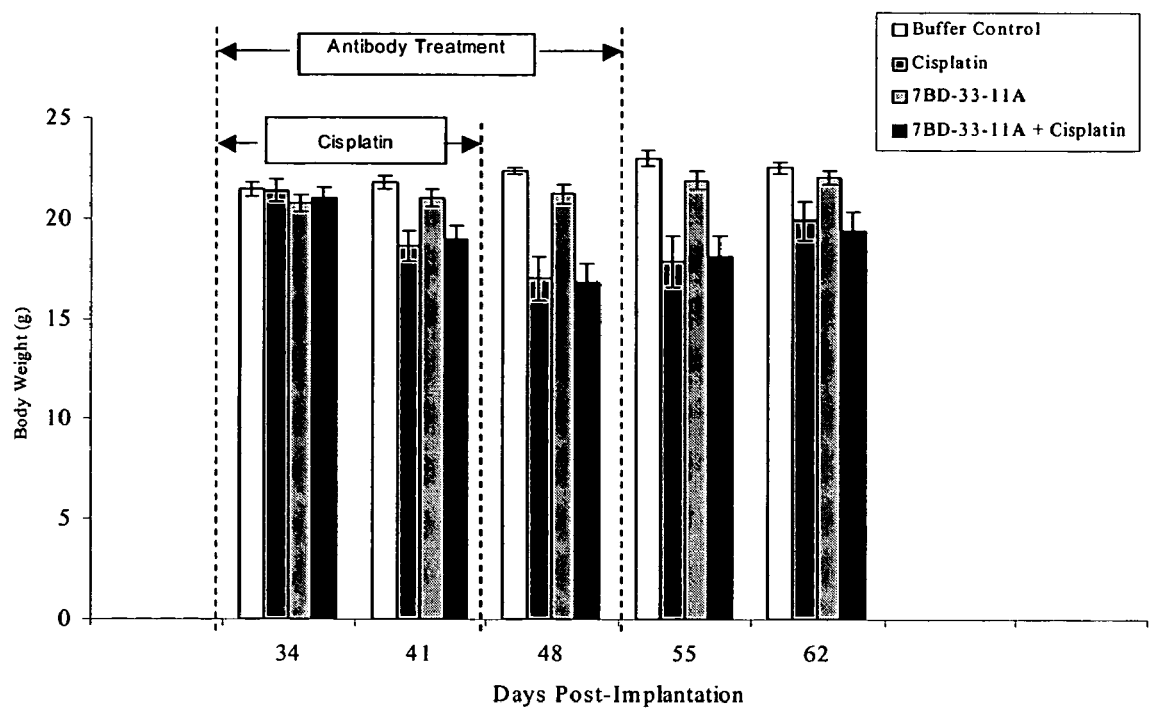
FIG. 20. Effect of 7BD-33-11A, Cisplatin, 7BD-33-11A+ Cisplatin or buffer control on body weight in an established MDA-MB-468 breast cancer model.

Representative histograms of 7BD-33-11A antibodies were compiled for FIG. 9. 7BD-33-11A displayed similar binding to cancer lines of breast (MB-231 and MCF-7), colon (HT-29, SW1116 and SW520), lung, ovary, pancreatic and prostate (PC-3) origin and differential binding to one of the breast (MB-468), colon (LOVO) and prostate (DU-145) cancer cell lines. There was also binding of 7BD-33-11A to non-cancer cells, however that binding did not produce cytotoxicity. This was further evidence that binding was not necessarily predictive of the outcome of antibody ligation of its cognate antigen, and was a non-obvious finding. This suggested that the context of antibody ligation in different cells was determinative of cytoxicity rather than just antibody binding.

TABLE 2

| | | BREAST | | | COLON | | | | LUNG | OVARY | | |
|---|---|---|---|---|---|---|---|---|---|---|---|---|
| Antibody | Isotype | MB-231 | MB-468 | MCF-7 | HT-29 | LOVO | SW1116 | SW620 | NCI H460 | ES-2 | OCC-1 | OVCAR |
| 7BD-33-11A | IgG2a, k | + | − | + | + | − | + | + | + | + | + | + |
| anti-EGFR | IgG1, k | ++ | ++ | − | + | − | + | − | + | + | + | + |

| | | PANCREATIC | PROSTATE | | NORMAL | | |
|---|---|---|---|---|---|---|---|
| Antibody | Isotype | BxPC-3 | DU-145 | PC-3 | CCD 27 sk | CCD-112 | Hs888 Lu |
| 7BD-33-11A | IgG2a, k | + | − | + | + | + | + |
| anti-EGFR | IgG1, k | + | + | + | + | + | + |

EXAMPLE 4

Normal Human Tissue Staining

IHC studies were previously conducted to characterize the 7BD-33-11A antigen distribution in humans (Ser. No. 10/603,006). The current studies compared 7BD-33-11A to two antibodies directed against CD63 (RFAC4 and H5C6) since the 7BD-33-11A antigen is CD63 as determined previously by biochemical methods. Binding of antibodies to 24 normal human tissues was performed using a human normal organ tissue array (Clinomics, Watervliet, N.Y.). All primary antibodies (7BD-33-11A; RFAC4 (Cymbus Biotechnology Ltd., Hants, UK) and H5C6 anti-CD63 (BD PharMingen, Oakville, ON); and mouse IgG$_1$ negative control (Dako, Toronto, ON)) were diluted in antibody dilution buffer (Dako, Toronto, ON) to a concentration of 5 µg/ml (found to be the optimal concentration in previous optimization steps). The negative control antibody has been shown to be negative to all mammalian tissues by the manufacturer. The procedure for IHC is as follows.

Tissue sections were deparaffinized by drying in an oven at 58° C. for 1 hr and dewaxed by immersing in xylene 5 times for 4 min each in Coplin jars. Following treatment through a series of graded ethanol washes (100%-75%) the sections were re-hydrated in water. The slides were immersed in 10 mM citrate buffer at pH 6 (Dako, Toronto, Ontario) then microwaved at high, medium, and low power settings for 5 min each and finally immersed in cold PBS. Slides were then immersed in 3% hydrogen peroxide solution for 6 min, washed with PBS three times for 5 min each, dried, incubated with Universal blocking solution (Dako, Toronto, Ontario) for 5 min at room temperature. 7BD-33-11A, monoclonal mouse anti-CD63 (Cymbus Biotechnology Ltd., Hants, UK or Dako, Toronto, Ontario) or isotype control antibody (directed towards *Aspergillus niger* glucose oxidase, an enzyme which is neither present nor inducible in mammalian tissues; Dako, Toronto, Ontario) were diluted in antibody dilution buffer (Dako, Toronto, Ontario) to its working concentration (5 µg/mL for each antibody) and incubated overnight for 1 hr at room temperature. The slides were washed with PBS 3 times for 5 minutes each. Immunoreactivity of the primary antibodies was detected/visualized with HRP conjugated secondary antibodies as supplied (Dako Envision System, Toronto, Ontario) for 30 minutes at room temperature. Following this step the slides were washed with PBS 3 times for 5 minutes each and a color reaction developed by adding DAB (3,3'-diaminobenzidine tetrahydrachloride, Dako, Toronto, Ontario) chromogen substrate solution for immunoperoxidase staining for 10 minutes at room temperature. Washing the slides in tap water terminated the chromogenic reaction. Following counterstaining with Meyer's Hematoxylin (Sigma Diagnostics, Oakville, ON), the slides were dehyrdated with graded ethanols (75-100%) and cleared with xylene. Using mounting media (Dako Faramount, Toronto, Ontario) the slides were coverslipped. Slides were microscopically examined using an Axiovert 200 (Zeiss Canada, Toronto, ON) and digital images acquired and stored using Northern Eclipse Imaging Software (Mississauga, ON). Results were read, scored and interpreted by a pathologist.

Table 3 presents a summary of the results of 7BD-33-11A and RFAC4 and H5C6 anti-CD63 staining of a test array of normal human tissues. The staining of tissues with 7BD-33-11A is similar to that described previously (Ser. No. 10/603,006). It should again be noted that 7BD-33-11A showed restricted binding to various cell types but had binding to infiltrating macrophages, lymphocytes, and fibroblasts. The RFAC4 and H5C6 antibodies showed a similar staining pattern in comparison to each other. However, the staining pattern of both RFAC4 and H5C6 was quite different than that observed with 7BD-33-11A. Specifically, both RFAC4 and H5C6 antibodies bound to a broader range of normal tissues, usually had higher staining intensity in tissues where 7BD-33-11A was also positive and bound not only to infiltrating macrophages, lymphocytes and fibroblasts and but to also to the epithelium in a majority of the tissues (FIG. 11).

Tissues that were positive for 7BD-33-11A were also positive for either RFAC4 or H5C6 anti-CD63 antibodies (sometimes with less intensity). Tissues that were negative for 7BD-33-11A were generally not negative for the RFAC4 or H5C6. These results demonstrated that 7BD-33-11A bound to a smaller subset of the tissues recognized by either the RFAC4 or H5C6 anti-CD63 antibody and within tissues the intensity of staining was also sometimes less. These results showed that the antigen for 7BD-33-11A was not widely expressed on normal tissues, and that the antibody bound specifically to a limited number of tissues in humans. It also supported the biochemical evidence that 7BD-33-11A was directed against an epitope of CD63, albeit to a different epitope than the one recognized by either the RFAC4 or H5C6 antibodies used for these IHC studies.

TABLE 3

Comparison of RFAC4 and H5C6 anti-CD63 and 7BD-33-11A IHC on Human Normal Tissue

| Section | Tissue | 7BD-33-11A | RFAC4 | H5C6 |
|---|---|---|---|---|
| Aa3 | Breast | — | + (Ductular epithelium and stromal fibroblasts) | +++ (Ductular epithelium and stromal fibroblasts) |
| Aa4 | Breast | +/− (2-3 stromal fibroblasts) *No staining of ductular epithelium | +/− (Ductular epithelium and stromal fibroblasts) | +++ (Stromal fibroblasts) +/− (Ductular epithelium) |
| Ab3 | Lung | +++ (Macrophages and fibroblasts at interalveolar septum) | +++ (Macrophages and fibroblasts at interalveolar septum) | +++ (Alveolar epithelium and macrophages) |
| Ab4 | Lung | +++ (Macrophages and fibroblasts at interalveolar septum) | +++ (Macrophages and fibroblasts at interalveolar septum) | +++ (Macrophages and fibroblasts at interalveolar septum) |
| Ab5 | Lung | +/− (Macrophages and fibroblasts at interalveolar septum) | +++ (Macrophages and fibroblasts at interalveolar septum) | +++ (Macrophages and fibroblasts at interalveolar septum) |
| Ac1 | Colon | +++ (Lymphocytes and macrophages in lamina propria) *No staining of Mucosal epithelium | +++ (Mucosal epithelium, lymphocytes and macrophages at lamina propria) | +++ (Mucosal epithelium, lymphocytes and macrophages at lamina propria) |
| Ac3 | Colon | — | — | +/− (Lymphocytes at lamina propria) |
| Ac4 | Colon | +++ (Macrophages and fibroblasts at lamina propria) + (Mucosal epithelium) | +++ (Macrophages and fibroblasts at lamina propria) + (Mucosal epithelium) | +++ (Mucosal epithelium, lymphocytes and macrophages at lamina propria) |
| Ac5 | Colon | +/− (Macrophages and fibroblasts at lamina propria) | +++ (Macrophages and fibroblasts at lamina propria) + (Mucosal epithelium) | +++ (Lymphocytes and macrophages in lamina propria) |
| Ad1 | Prostate | +++ (Glandular epithelium) | +++ (Glandular epithelium) | +++ (Glandular epithelium) |
| Ad2 | Prostate | +++ (Glandular epithelium) | +++ (Glandular epithelium) | +++ (Glandular epithelium) |

TABLE 3-continued

Comparison of RFAC4 and H5C6 anti-CD63 and 7BD-33-11A IHC on Human Normal Tissue

| Section | Tissue | 7BD-33-11A | RFAC4 | H5C6 |
|---------|--------|------------|-------|------|
| Ad4 | Prostate | ++ (Glandular epithelium) | | +++ (Glandular epithelium) |
| Ad5 | Prostate | +++ (Glandular epithelium) | +++ (Glandular epithelium) | +++ (Glandular epithelium) |
| Ae1 | Kidney | — | + (Tubular epithelium) | ++ (Tubular epithelium) |
| Ae2 | Kidney | +/− (2-3 interstitial cells) *No staining of tubular epithelium | ++ (Tubular epithelium) | ++ (Tubular epithelium) |
| Ae3 | Kidney | +/− (2-3 interstitial cells) | ++ (Tubular epithelium) | ++ (Tubular epithelium) |
| Ae4 | Liver | ++ (Hepatocytes and sinusoidal staining) | +++ (Hepatocytes & sinusoidal staining and bile duct epithelium) | +++ (Hepatocytes, sinusoidal staining and bile ducts) |
| Af1 | Liver | — | ++ (Sinusoidal and bile duct epithelium) | ++ (Sinusoidal and bile duct epithelium) |
| Af2 | Liver | — | +/− (Hepatocytes and sinusoidal staining) | +/− (Hepatocytes and sinusoidal staining) |
| Af3 | Lymph node | — | ++ (Reticular cells) | ++ (Reticular cells) |
| Ag1 | Thyroid | — | +/− (Follicular cells) | +/− (Follicular cells) |
| Ag2 | Thyroid | +++ (Follicular cells) | +++ (Follicular cells) | +++ (Follicular cells) |
| Ah1 | Placenta | — | +++ (Syncytiotrophoblasts & basement membrane of chorionic villi) | +++ (Syncytiotrophoblasts & basement membrane of chorionic villi) |
| Ah2 | Placenta | — | +++ (Syncytiotrophoblasts & basement membrane of chorionic villi) | +++ (Syncytiotrophoblasts & basement membrane of chorionic villi) |

EXAMPLE 5

Human Breast Tumor Tissue Staining

A previous IHC study was undertaken to determine the cancer association of the 7BD-33-11A antigen with human breast cancers and whether the 7BD-33-11A antibody was likely to recognize human cancers (Ser. No. 10/603,006). Currently, a comparison was carried out using RFAC4 and H5C6 anti-CD63 and c-erbB-2 anti-Her2 antibodies. A breast cancer tissue array derived from 50 breast cancer patients and 10 samples derived from non-neoplastic breast tissue in breast cancer patients was used (Imgenex Corporation, San Diego, Calif.). The following information was provided for each patient: age, sex, American Joint Committee on Cancer (AJCC) tumor stage, lymph node, estrogen receptor (ER) and projesterone receptor (PR) status. The procedure for IHC from Example 4 was followed. All antibodies were used at a working concentration of 5 μg/mL except for the anti-Her2 antibody where a concentration of 1.5 μg/mL was used.

Tables 4, 5 and 6 and 7 provide summaries of 7BD-33-11A, RFAC4 and H5C6 anti-CD63 antibody staining of breast cancer tissue arrays. Overall, 36 percent of the 50 patients tested were positive for 7BD-33-11A antigen compared to 85 and 94 percent for RFAC4 and H5C6 anti-CD63 antibodies respectively. In cases where both 7BD-33-11A and RFAC4 or H5C6 anti-CD63 antibodies stained the same tissue, 97 percent of the samples had higher intensity staining with both the RFAC4 and H5C6 anti-CD63 in comparison to 7BD-33-11A (FIG. 12). For 7BD-33-11A 0 out of 10 and for both RFAC4 and H5C6 anti-CD63 antigen 7 out of 8 (2 samples were not representative) normal breast tissue samples from breast cancer patients were positive, respectively. There was a slight correlation between estrogen or progesterone receptor expression and expression of 7BD-33-11A antigen; tissues with either receptor expression had slightly higher 7BD-33-11A antigen expression. When tumors were analyzed based on their stage, or degree to which the cancer advanced, results suggested a trend towards greater positive expression with higher tumor stage for 7BD-33-11A. Similar results were obtained with RFAC4. H5C6 also showed a very slight correlation with estrogen or progesterone receptor expression but there was no apparent correlation with tumor stage. However, for all three antibodies, the results were limited by the small sample size.

TABLE 4

Human Breast Tumor IHC Summary for 7BD-33-11A

| | | | Binding Score | | | | | | % positive |
|---|---|---|---|---|---|---|---|---|---|
| | | Total # | − | +/− | + | ++ | +++ | Total positive | of total |
| Patient | Tumor | 50 | 32 | 10 | 4 | 3 | 1 | 18 | 36% |
| Samples | Normal | 10 | 10 | 0 | 0 | 0 | 0 | 0 | 0% |
| ER Status | ER+ | 28 | 16 | 9 | 1 | 2 | 0 | 12 | 43% |
| | ER− | 22 | 15 | 3 | 2 | 1 | 1 | 7 | 32% |
| | Unknown | 0 | 0 | 0 | 0 | 0 | 0 | 0 | 0% |
| PR Status | PR+ | 19 | 9 | 6 | 2 | 2 | 0 | 10 | 53% |
| | PR− | 30 | 20 | 6 | 2 | 1 | 1 | 10 | 33% |
| | Unknown | 1 | 1 | 0 | 0 | 0 | 0 | 0 | 0% |
| AJCC Tumor | T1 | 4 | 4 | 0 | 0 | 0 | 0 | 0 | 0% |
| Stage | T2 | 21 | 14 | 3 | 2 | 1 | 1 | 7 | 33% |
| | T3 | 20 | 11 | 6 | 2 | 1 | 0 | 9 | 45% |
| | T4 | 5 | 1 | 3 | 0 | 1 | 0 | 4 | 80% |

TABLE 5

Human Breast Tumor IHC Summary for RFAC4

| | | Total # | Binding Score | | | | | Total positive | % positive of total |
|---|---|---|---|---|---|---|---|---|---|
| | | | − | +/− | + | ++ | +++ | | |
| Patient | Tumor | 47 | 7 | 3 | 7 | 16 | 14 | 40 | 85% |
| Samples | Normal | 8 | 1 | 1 | 0 | 2 | 4 | 7 | 87.50% |
| ER Status | ER+ | 27 | 1 | 2 | 3 | 15 | 6 | 26 | 96% |
| | ER− | 20 | 6 | 1 | 3 | 4 | 6 | 14 | 70% |
| | Unknown | 0 | 0 | 0 | 0 | 0 | 0 | 0 | 0% |
| PR Status | PR+ | 18 | 0 | 1 | 2 | 9 | 6 | 18 | 100% |
| | PR− | 28 | 7 | 2 | 4 | 9 | 6 | 21 | 75% |
| | Unknown | 1 | 0 | 0 | 0 | 1 | 0 | 1 | 100% |
| AJCC Tumor | T1 | 4 | 2 | 0 | 1 | 1 | 0 | 2 | 50% |
| Stage | T2 | 20 | 4 | 2 | 3 | 6 | 5 | 16 | 80% |
| | T3 | 18 | 1 | 1 | 2 | 7 | 7 | 17 | 94% |
| | T4 | 5 | 0 | 0 | 1 | 2 | 2 | 5 | 100% |

TABLE 6

Human Breast Tumor IHC Summary for H5C6

| | | Total # | Binding Score | | | | | Total positive | % positive of total |
|---|---|---|---|---|---|---|---|---|---|
| | | | − | +/− | + | ++ | +++ | | |
| Patient | Tumor | 47 | 3 | 4 | 8 | 15 | 17 | 44 | 94% |
| Samples | Normal | 8 | 1 | 1 | 0 | 2 | 4 | 7 | 87.50% |
| ER Status | ER+ | 27 | 1 | 1 | 6 | 8 | 11 | 26 | 96% |
| | ER− | 20 | 2 | 3 | 2 | 8 | 5 | 18 | 90% |
| | Unknown | 0 | 0 | 0 | 0 | 0 | 0 | 0 | 0% |
| PR Status | PR+ | 18 | 0 | 0 | 4 | 4 | 10 | 18 | 100% |
| | PR− | 28 | 3 | 4 | 4 | 11 | 6 | 25 | 89% |
| | Unknown | 1 | 0 | 0 | 0 | 1 | 0 | 1 | 100% |
| AJCC Tumor | T1 | 4 | 0 | 0 | 1 | 2 | 1 | 4 | 100% |
| Stage | T2 | 20 | 2 | 4 | 3 | 7 | 4 | 18 | 90% |
| | T3 | 18 | 1 | 0 | 3 | 4 | 10 | 17 | 94% |
| | T4 | 5 | 0 | 0 | 1 | 2 | 2 | 5 | 100% |

The 7BD-33-11A staining was specific for cancerous cells in comparison to normal cells where stromal cells were clearly negative and sheets of malignant cells were positive. The cellular localization pattern seen with the 7BD-33-11A antigen was confined to the cell membrane and cytoplasm. Similar membranous and cytoplasmic staining results were obtained with the anti-CD63 antibodies, RFAC4 and H5C6 on the breast tumor tissue samples. Additionally, both of these antibodies showed this staining localization pattern on normal breast tissue samples whereas 7BD-33-11A was negative.

In comparison to c-erbB-2, 7BD-33-11A showed a completely different staining profile where 9 out of the 18 breast tumor tissue samples that were positive for the 7BD-33-11A antigen were negative for Her2 expression indicating a yet unmet targeted therapeutic need for breast cancer patients (Table 8, FIG. 13). There were also differences in the intensity of staining between the breast tumor tissue sections that were positive for both 7BD-33-11A and Her2; some breast tumor tissue sections that were highly positive for the 7BD-33-11A antigen were only mildly positive for Her2 and vice versa again illustrating that 7BD-33-11A would therapeutically target a different cohort of breast cancer patients. The c-erbB-2 antibody also positively stained one of the normal breast tissue sections.

These results suggested the antigen for 7BD-33-11A may be expressed by approximately two thirds of breast cancer patients and half of those were completely negative for the Her2 antigen. The staining pattern showed that in patient samples, the antibody is highly specific for malignant cells and the 7BD-33-11A antigen was present on the cell membrane thereby making it an attractive drugable target. The similar albeit much more limited staining of 7BD-33-11A versus either the RFAC4 or H5C6 anti-CD63 antibody again demonstrates the likelihood of the 7BD-33-11A epitope being a more restrictive epitope on CD63.

TABLE 7

Comparison of RFAC4 and H5C6 anti-CD63 and 7BD-33-11A IHC on Human Tumor and Normal Breast Tissue

| Data sheet | | | | RFAC4 | H5C6 | 7BD-33-11A |
|---|---|---|---|---|---|---|
| Sec. No. | Sex | Age | Diagnosis | Section Score | Section Score | Section Score |
| 1 | F | 28 | Infiltrating duct carcinoma | +++ | +++ | ++ |
| 2 | F | 71 | Solid papillary carcinoma | +++ | +++ | +/− |

TABLE 7-continued

Comparison of RFAC4 and H5C6 anti-CD63 and 7BD-33-11A IHC on Human Tumor and Normal Breast Tissue

| | | | Data sheet | RFAC4 | H5C6 | 7BD-33-11A |
|---|---|---|---|---|---|---|
| Sec. No. | Sex | Age | Diagnosis | Section Score | Section Score | Section Score |
| 3 | F | 26 | Infiltrating duct carcinoma | ++ | + | − |
| 4 | F | 43 | Infiltrating duct carcinoma | ++ | ++ | +/− |
| 5 | F | 39 | Infiltrating duct carcinoma | NR | NR | +/− |
| 6 | F | 46 | Ductal carcinoma in situ | + | + | +/− |
| 7 | F | 47 | Infiltrating duct carcinoma | +++ | +++ | + |
| 8 | M | 67 | Infiltrating duct carcinoma | +++ | +++ | + |
| 9 | F | 33 | Infiltrating duct carcinoma | +++ | +++ | − |
| 10 | F | 47 | Infiltrating duct carcinoma | ++ | ++ | − |
| 11 | F | 49 | Invasive lobular carcinoma | − | − | − |
| 12 | F | 46 | Infiltrating duct carcinoma | ++ | ++ | − |
| 13 | F | 39 | Infiltrating duct carcinoma | ++ | ++ | − |
| 14 | F | 43 | Infiltrating lobular carcinoma | +++ | +++ | +/− |
| 15 | F | 54 | Infiltrating lobular carcinoma | ++ | ++ | +/− |
| 16 | F | 58 | Infiltrating duct carcinoma | + | ++ | +/− |
| 17 | F | 37 | Infiltrating duct carcinoma | +++ | ++ | − |
| 18 | F | 43 | Infiltrating duct carcinoma | +++ | +++ | +++ |
| 19 | F | 51 | Infiltrating duct carcinoma | +++ | +++ | + |
| 20 | F | 80 | Medullary carcinoma | ++ | ++ | − |
| 21 | F | 36 | Infiltrating duct carcinoma | NR | NR | − |
| 22 | F | 59 | Infiltrating duct carcinoma | + | + | − |
| 23 | F | 34 | Ductal carcinoma in situ | +++ | +++ | + |
| 24 | F | 54 | Infiltrating duct carcinoma | ++ | +++ | +/− |
| 25 | F | 47 | Infiltrating duct carcinoma | +++ | +++ | ++ |
| 26 | F | 53 | Infiltrating duct carcinoma | ++ | ++ | − |
| 27 | F | 59 | Infiltrating duct carcinoma | + | + | − |
| 28 | F | 60 | Signet ring cell carcinoma | F | F | − |
| 29 | F | 37 | Infiltrating duct carcinoma | +++ | +++ | ++ |
| 30 | F | 46 | Infiltrating duct carcinoma | ++ | ++ | +/− |
| 31 | F | 35 | Infiltrating duct carcinoma | − | − | − |
| 32 | F | 47 | Infiltrating duct carcinoma | ++ | ++ | − |
| 33 | F | 54 | Infiltrating duct carcinoma | + | + | − |
| 34 | F | 47 | Infiltrating duct carcinoma | − | +/− | − |
| 35 | F | 41 | Infiltrating duct carcinoma | +++ | +++ | − |
| 36 | F | 38 | Infiltrating duct carcinoma | +++ | +++ | − |
| 37 | F | 55 | Infiltrating duct carcinoma | − | +/− | − |
| 38 | F | 65 | Infiltrating duct carcinoma | +/− | +/− | − |
| 39 | M | 66 | Infiltrating duct carcinoma | − | + | − |
| 40 | F | 44 | Infiltrating duct carcinoma | ++ | +++ | − |
| 41 | F | 52 | Metastatic carcinoma in lymph node | ++ | ++ | − |
| 42 | F | 32 | Metastatic carcinoma in lymph node | +/− | + | − |
| 43 | F | 58 | Metastatic carcinoma in lymph node | ++ | +++ | +/− |
| 44 | F | 52 | Metastatic carcinoma in lymph node | + | + | − |
| 45 | F | 58 | Metastatic carcinoma in lymph node | − | − | − |
| 46 | F | 38 | Metastatic carcinoma in lymph node | ++ | +++ | − |
| 47 | F | 45 | Metastatic carcinoma in lymph node | − | ++ | − |
| 48 | F | 45 | Metastatic carcinoma in lymph node | ++ | ++ | − |
| 49 | F | 29 | Metastatic carcinoma in lymph node | +/− | +/− | − |
| 50 | F | 61 | Metastatic carcinoma in lymph node | + | ++ | − |
| 51 | F | 46 | Nipple | ++ | ++ | − |
| 52 | F | 47 | Nipple | NR | NR | − |
| 53 | F | 40 | Normal breast | +/− | +/− | − |
| 54 | F | 43 | Normal breast | +++ | +++ | − |
| 55 | F | 40 | Normal breast | ++ | +++ | − |
| 56 | F | 40 | Normal breast | +++ | ++ | − |
| 57 | F | 45 | Normal breast | NR | NR | − |
| 58 | F | 44 | Normal breast | − | − | − |
| 59 | F | 37 | Normal breast | +++ | +++ | − |
| 60 | F | 51 | Normal breast | +++ | +++ | − |

Abbreviations:
NR: the sample is not representative and
F: the section is folded.

TABLE 8

Comparison of c-erbB-2 anti-Her2 and 7BD-33-11A IHC on Human Tumor and Normal Breast Tissue

| | Data sheet | | | c-erbB-2 | 7BD-33-11A |
|---|---|---|---|---|---|
| Sec. No. | Sex | Age | Diagnosis | Section Score | Section Score |
| 1 | F | 28 | Infiltrating duct carcinoma | + | ++ |
| 2 | F | 71 | Solid papillary carcinoma | − | +/− |
| 3 | F | 26 | Infiltrating duct carcinoma | +/− | − |
| 4 | F | 43 | Infiltrating duct carcinoma | +/− | +/− |
| 5 | F | 39 | Infiltrating duct carcinoma | NR | +/− |
| 6 | F | 46 | Ductal carcinoma in situ | − | +/− |
| 7 | F | 47 | Infiltrating duct carcinoma | +++ | + |
| 8 | M | 67 | Infiltrating duct carcinoma | − | + |
| 9 | F | 33 | Infiltrating duct carcinoma | +++ | − |
| 10 | F | 47 | Infiltrating duct carcinoma | ++ | − |
| 11 | F | 49 | Invasive Lobular carcinoma | PD | − |
| 12 | F | 46 | Infiltrating duct carcinoma | − | − |
| 13 | F | 39 | Infiltrating duct carcinoma | +++ | − |
| 14 | F | 43 | Infiltrating lobular carcinoma | − | +/− |
| 15 | F | 54 | Infiltrating lobular carcinoma | − | +/− |
| 16 | F | 58 | Infiltrating duct carcinoma | − | +/− |
| 17 | F | 37 | Infiltrating duct carcinoma | +++ | − |
| 18 | F | 43 | Infiltrating duct carcinoma | − | +++ |
| 19 | F | 51 | Infiltrating duct carcinoma | + | + |
| 20 | F | 80 | Medullary carcinoma | − | − |
| 21 | F | 36 | Infiltrating duct carcinoma | NR | − |
| 22 | F | 59 | Infiltrating duct carcinoma | − | − |
| 23 | F | 34 | Ductal carcinoma in situ | +++ | + |
| 24 | F | 54 | Infiltrating duct carcinoma | + | +/− |
| 25 | F | 47 | Infiltrating duct carcinoma | − | ++ |
| 26 | F | 53 | Infiltrating duct carcinoma | +++ | − |
| 27 | F | 59 | Infiltrating duct carcinoma | + | − |
| 28 | F | 60 | Signet ring cell carcinoma | − | − |
| 29 | F | 37 | Infiltrating duct carcinoma | +++ | ++ |
| 30 | F | 46 | Infiltrating duct carcinoma | − | +/− |
| 31 | F | 35 | Infiltrating duct carcinoma | − | − |
| 32 | F | 47 | Infiltrating duct carcinoma | +++ | − |
| 33 | F | 54 | Infiltrating duct carcinoma | − | − |
| 34 | F | 47 | Infiltrating duct carcinoma | +++ | − |
| 35 | F | 41 | Infiltrating duct carcinoma | − | − |
| 36 | F | 38 | Infiltrating duct carcinoma | ++ | − |
| 37 | F | 55 | Infiltrating duct carcinoma | +/− | − |
| 38 | F | 65 | Infiltrating duct carcinoma | − | − |
| 39 | M | 66 | Infiltrating duct carcinoma | − | − |
| 40 | F | 44 | Infiltrating duct carcinoma | − | − |
| 41 | F | 52 | Metastatic carcinoma in Lymph node | − | − |
| 42 | F | 32 | Metastatic carcinoma in Lymph node | − | − |
| 43 | F | 58 | Metastatic carcinoma in Lymph node | ++ | +/− |
| 44 | F | 52 | Metastatic carcinoma in Lymph node | +++ | − |
| 45 | F | 58 | Metastatic carcinoma in Lymph node | − | − |
| 46 | F | 38 | Metastatic carcinoma in Lymph node | ++ | − |
| 47 | F | 45 | Metastatic carcinoma in Lymph node | − | − |
| 48 | F | 45 | Metastatic carcinoma in Lymph node | − | − |
| 49 | F | 29 | Metastatic carcinoma in Lymph node | − | − |
| 50 | F | 61 | Metastatic carcinoma in Lymph node | − | − |
| 51 | F | 46 | Nipple | − | − |
| 52 | F | 47 | Nipple | +++ | − |
| 53 | F | 40 | Normal Breast | − | − |
| 54 | F | 43 | Normal Breast | − | − |
| 55 | F | 40 | Normal Breast | +/− | − |
| 56 | F | 40 | Normal Breast | − | − |
| 57 | F | 45 | Normal Breast | − | − |
| 58 | F | 44 | Normal Breast | − | − |
| 59 | F | 37 | Normal Breast | − | − |
| 60 | F | 51 | Normal Breast | − | − |

EXAMPLE 6

Human Prostate Tissue Staining

To determine whether the 7BD-33-11A antigen was expressed on other human cancer tissues in addition to breast cancer, a multiple human tumor tissue array was probed with 7BD-33-11A (Ser. No. 10/603,006; Imgenex, San Diego, Calif.). In furthering those studies, the staining pattern of 7BD-33-11A was determined on a human prostate tumor tissue array (Imgenex Corporation, San Diego, Calif.). The staining procedure used was the same as the one outlined in Example 4. All antibodies were used at a working concentration of 5 µg/mL.

As outlined in Table 9, 7BD-33-11A stained 88 percent of human prostate cancers. Although 7BD-33-11A stained the normal tissue sections with high intensity as well, there was a higher degree of membranous staining in the tumor tissue samples in comparison to the normal samples. There was one embryonal rhabdomyosarcroma tissue sample that did not stain for the 7BD-33-11A antigen. There also appeared to be no direct correlation between tumor stage and presence of the 7BD-33-11A antigen. However, the results were limited by the small sample size. Again with 7BD-33-11A there was both membranous and cytoplasmic staining observed on the prostate tumor tissue samples. However, there was an increase in the degree of membranous staining relative to that seen with the breast tumor tissue samples (FIG. 14). For the normal prostate tissue samples, this increase in the degree of membranous staining was not observed.

TABLE 9

Human Prostate Tumor IHC Summary for 7BD-33-11A

| | | | Binding Score | | | | | | % of positive |
|---|---|---|---|---|---|---|---|---|---|
| | | Total # | − | +/− | + | ++ | +++ | Total positive | of total |
| Patients' Sample | Tumor | 51 | 6 | 6 | 6 | 7 | 26 | 45 | 88% |
| | Normal | 3 | 0 | 0 | 0 | 1 | 2 | 3 | 100% |

TABLE 9-continued

Human Prostate Tumor IHC Summary for 7BD-33-11A

|  |  | Total # | Binding Score | | | | | Total positive | % of positive of total |
|---|---|---|---|---|---|---|---|---|---|
|  |  |  | − | +/− | + | ++ | +++ |  |  |
| Tumor Subtype | Adenocarcinoma | 50 | 5 | 6 | 6 | 7 | 26 | 44 | 88% |
|  | embryonal Rhabdomyosarcoma | 1 | 1 | 0 | 0 | 0 | 0 | 0 | 0% |
| Tumor Stage | I | 1 | 0 | 0 | 0 | 0 | 1 | 1 | 100% |
|  | II | 11 | 0 | 0 | 1 | 3 | 7 | 11 | 100% |
|  | III | 2 | 1 | 0 | 0 | 0 | 1 | 1 | 50% |
|  | IV | 32 | 6 | 5 | 5 | 3 | 13 | 26 | 81% |

Therefore, it appeared that the 7BD-33-11A antigen was not solely found on the membranes of breast cancers but also on the membrane of prostate cancers. These results indicated that 7BD-33-11A has potential as a therapeutic drug in tumor types besides breast.

The preponderance of evidence shows that 7BD-33-11A mediates anti-cancer effects through ligation of a conformational epitope present on a variant of CD63. It has been shown, in Example 2, 7BD-33-11A antibody can be used to inmunoprecipitate the cognate antigen from expressing cells such as MDA-MB-231 cells. Further it could be shown that the 7BD-33-11A antibody could be used in detection of cells and/or tissues which express a CD63 antigenic moiety which specifically binds thereto, utilizing techniques illustrated by, but not limited to FACS, cell ELISA or IHC.

Thus, it could be shown that the immunoprecipitated 7BD-33-11A antigen can inhibit the binding of 7BD-33-11A to such cells or tissues using such FACS, cell ELISA or IHC assays. Further, as with the 7BD-33-11A antibody, other anti-CD63 antibodies could be used to immunoprecipitate and isolate other forms of the CD63 antigen, and the antigen can also be used to inhibit the binding of those antibodies to the cells or tissues that express the antigen using the same types of assays.

EXAMPLE 7

In Vivo MDA-MB-231 Preventative Dose Response Tumor Experiments

With reference to the data shown in FIGS. 15 and 16, 6 to 8 week old, female SCID mice were implanted with 5 million MDA-MB-231 human breast cancer cells in 100 microliters saline injected subcutaneously in the scruff of the neck. The mice were randomly divided into 4 treatment groups of 10. On the day after implantation 0.2, 2.0 or 20 mg/kg of 7BD-33-11A or 20 mg/kg IgG isotype control antibody was administered intraperitoneally at a volume of 300 microliters after dilution from the stock concentration with a diluent that contained 2.7 mM KCl, 1 mM $KH_2PO_4$, 137 mM NaCl and 20 mM $Na_2HPO_4$. The antibodies were then administered once per week for a period of 7 weeks in the same fashion. Tumor growth was measured about every 7th day with calipers or until individual animals reached the CCAC end-points. Body weights of the animals were recorded for the duration of the study.

At the end of treatment (day 55), the 0.2 mg/kg treatment group had tumor growth that was 15 percent of the isotype control group. The 85 percent reduction in tumor growth in the 0.2 mg/kg 7BD-33-11A treatment group was determined to be a significant difference in comparison to the isotype control as determined by a paired t-test (p<0.0001). Both of the 2.0 and 20 mg/kg treatment groups had yet to develop tumors by the end of treatment (day 55). This trend continued on well beyond the treatment period. Treatment with 7BD-33-11A antibody, at all doses, also led to an increase in survival in comparison to the isotype control treated group. All of the mice in control treated group had died by day 104 (54 days after treatment). By contrast, the mice in the 0.2 mg/kg group survived until day 197 (147 days after treatment), 50 percent of the mice in the 2.0 mg/kg treatment group were sill alive at day 290 (240 days after treatment) and 100 percent of the 20 mg/kg group were also still alive at also day 290. Therefore, 7BD-33-11A treatment, at all 3 doses, significantly reduced tumor burden and increased survival in comparison to an isotype control antibody. Treatment at the highest dose demonstrated the greatest reduction in tumor growth (100 percent) and the largest increase in survival (all mice are still alive). Consequently, 7BD-33-11A is a potent anti-tumor antibody suggesting pharmacologic and pharmaceutical benefits of this antibody for therapy in other mammals, including man.

EXAMPLE 8

In Vivo MDA-MB-231 Established Chemotherapy Combination Tumor Experiments

With reference to FIGS. 17 and 18, 6 to 8 week old female SCID mice were implanted with 5 million MDA-MB-231 human breast cancer cells in 100 microlitres saline injected subcutaneously in the scruff of the neck. Tumor growth was measured with calipers every week. When the majority of the cohort reached a tumor volume of 100 mm³ (range 48-122 mm³) at 41 days post-implantation 8 mice were randomly assigned into each of 4 treatment groups. 7BD-33-11A antibody, the chemotherapeutic drug Cisplatin, the combination of 7BD-33-11A and Cisplatin or buffer control was administered intraperitoneally with 10 or 9 mg/kg of antibody or Cisplatin respectively at a volume of 300 microliters after dilution from the stock concentration with a diluent that contained 2.7 mM KCl, 1 mM $KH_2PO_4$, 137 mM NaCl and 20 mM $Na_2HPO_4$. 7BD-33-11A or buffer control was then administered 3 times per week for 10 doses in total in the same fashion until day 64 post-implantation. Cisplatin was administered on days 1, 3 and 9 of the treatment period. Tumor growth was measured about every seventh day with calipers until day 125 post-implantation or until individual animals reached the CCAC end-points. Body weights of the animals were recorded for the duration of the study. At the end of the study all animals were euthanised according to CCAC guidelines.

Using a paired t-test, there was a post-treatment tumor burden reduction (FIG. 16) associated with treatment with either 7BD-33-11A, Cisplatin or the combination of the two. At day 69 (5 days post-treatment) both 7BD-33-11A, Cisplatin and the antibody-drug combination had decreased mean tumor volumes compared to buffer control treatment;

76 (p<0.001), 79 (p<0.001) and 86 percent (p<0.001) respectively. Body weight was used as a surrogate for well-being. Although both Cisplatin and 7BD-33-11A displayed similar tumor suppression, there was not the same degree of weight loss seen with Cisplatin treatmentin comparison to treatment with the 7BD-33-11A antibody. There was little difference between the buffer control and 7BD-33-11A treated groups over the time points monitored. In fact, groups treated with the buffer control and 7BD-33-11A showed a slight weight gain after the treatment period. In contrast, the groups treated with Cisplatin experienced a weight loss that was especially evident after administration of the final dose. On day 55 post-implantation (4 days after the final dose of Cisplatin), the Cisplatin treated groups showed a 24-30 percent loss in body weight. Therefore both 7BD-33-11A and Cisplatin lowered the tumor burden in comparison to a buffer control in a well-recognized model of human breast cancer disease. However, 7BD-33-11A treated animals experienced better well-being than the Cisplatin treatment group as measured by body weight. These results suggest pharmacologic, pharmaceutical and quality of life benefits of this antibody for therapy in other mammals, including man.

EXAMPLE 9

In Vivo MDA-MB468 Established Chemotherapy Combination Tumor Experiments

With reference to FIGS. 19 and 20, 6 to 8 week old female SCID mice were implanted with 2 million MDA-MB-468 human breast cancer cells in 100 microlitres saline injected subcutaneously in the scruff of the neck. Tumor growth was measured with calipers every week. When the majority of the cohort reached a tumor volume of 100 $mm^3$ (range 11-119 $mm^3$) at 27 days post-implantation 8 mice were randomly assigned into each of 4 treatment groups. 7BD-33-11A antibody, the chemotherapeutic drug Cisplatin, the combination of 7BD-33-11A and Cisplatin or buffer control was administered intraperitoneally with 10 or 6 mg/kg of antibody or Cisplatin respectively at a volume of 300 microliters after dilution from the stock concentration with a diluent that contained 2.7 mM KCl, 1 mM $KH_2PO_4$, 137 mM NaCl and 20 mM $Na_2HPO_4$. 7BD-33-11A or buffer control was then administered 4 times per week for the first week followed by 3 times per week for 11 doses in total in the same fashion until day 50 post-implantation. Cisplatin was administered on days 1, 6, 11 and 16 of the treatment period. Tumor growth was measured about every seventh day with calipers until day 66 post-implantation or until individual animals reached the CCAC end-points. Body weights of the animals were recorded for the duration of the study. At the end of the study all animals were euthanised according to CCAC guidelines.

Using a paired t-test, there was a post-treatment tumor burden reduction (FIG. 18) associated with treatment with either 7BD-33-11A or Cisplatin or the combination of the two. At day 55 (5 days post-treatment) both 7BD-33-11A, Cisplatin and the antibody-drug combination had decreased mean tumor volumes compared to buffer control treatment; 37 (p=0.3958), 95 (p=0.024) and 97 percent (p=0.017) respectively. Body weight was used as a surrogate for well-being. Although both 7BD-33-11A and, to a greater extent, Cisplatin displayed tumor suppression, there was not the same degree of weight loss seen with 7BD-33-11A antibody treatment in comparison to Cisplatin treatment. There was little difference between the buffer control and the 7BD-33-11A treated groups over the time points monitored. In fact, groups treated with the buffer control and 7BD-33-11A showed some slight weight gain during the treatment period. In contrast, the groups treated with Cisplatin experienced a weight loss that was especially evident after the final dose of Cisplatin was administered. On day 48 post-implantation (4 days after the final dose of Cisplatin), the Cisplatin treated groups showed a 20 percent loss in body weight. Therefore both 7BD-33-11A and Cisplatin lowered the tumor burden in comparison to a buffer control in another well-recognized model of human breast cancer disease. However, 7BD-33-11A treated animals experienced better well-being than the Cisplatin treatment group as measured by body weight. In all, these results in which 7BD-33-11A produced significant benefits (improved survival, decreased tumor burden in comparison to control treatment, and better tolerability in comparison to chemotherapy) in mulitple models of human cancer suggest pharmacologic, pharmaceutical and quality of life benefits of this antibody for therapy in other mammals, including man.

The preponderance of evidence shows that 7BD-33-11A mediates anti-cancer effects through ligation of an epitope present on extracellular loop 2 on CD63. It has been shown, in Example 2, 7BD-33-11A antibody can be used to immunoprecipitate the cognate antigen from expressing cells such as MDA-MB-231 cells. Further it could be shown that the 7BD-33-11A antibody could be used in detection of cells and/or tissues which express a CD63 antigenic moiety which specifically binds thereto, utilizing techniques illustrated by, but not limited to FACS, cell ELISA or IHC.

Thus, it could be shown that the immunoprecipitated 7BD-33-11A antigen can inhibit the binding of 7BD-33-11A to such cells or tissues using FACS, cell ELISA or IHC assays. Further, as with the 7BD-33-11A antibody, other anti-CD63 antibodies could be used to immunoprecipitate and isolate other forms of the CD63 antigen, and the antigen can also be used to inhibit the binding of those antibodies to the cells or tissues that express the antigen using the same types of assays.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

---

What is claimed is:

1. A method for treating a patient suffering from human breast or prostate cancer comprising:

administering to said patient an isolated monoclonal antibody or antigen binding fragment thereof, said antibody or antigen binding fragment thereof characterized as being cytotoxic against cells of said breast or prostate cancer;

wherein said antibody or antigen binding fragment thereof is placed in admixture with a pharmaceutically acceptable adjuvant and is administered in an amount effective to mediate treatment of said breast or prostate cancer;

said antibody being an isolated monoclonal antibody or antigen binding fragment thereof which binds to the same epitope as that bound by the isolated monoclonal antibody produced by the hybridoma cell line deposited with the ATCC as PTA-4890.

2. The method for treating a patient suffering from breast or prostate cancer in accordance with claim 1, wherein said isolated monoclonal antibody or antigen binding fragment thereof is humanized.

3. The method for treating a patient suffering from breast or prostate cancer in accordance with claim 1 comprising:
   conjugating said antibody or antigen binding fragment thereof with a member selected from the group consisting of toxins, radioactive compounds, and hematogenous cells, thereby forming an antibody conjugate; and
   administering said antibody conjugate or conjugated antigen binding fragments thereof to said patient;
   wherein said antibody conjugate or conjugated antigen binding fragments are placed in admixture with a pharmaceutically acceptable adjuvant and are administered in an amount effective to mediate treatment of said breast or prostate cancer.

4. The method of claim 3, wherein said antibody or antigen binding fragment thereof is humanized.

5. The method for treating a patient suffering from breast or prostate cancer in accordance with claim 1 wherein:
   said method of production is performed with a tissue sample containing cancerous and non-cancerous cells obtained from said patient.

6. A method for treating a patient suffering from human breast or prostate cancer comprising:
   administering to said patient an isolated monoclonal antibody or antigen binding fragment thereof, said isolated monoclonal antibody being cytotoxic against cells of said breast or prostate cancer;
   wherein said antibody is the isolated monoclonal antibody produced by the hybridoma cell line deposited with the ATCC as PTA4890 or an antigen binding fragment thereof, and is placed in admixture with a pharmaceutically acceptable adjuvant and is administered in an amount effective to mediate treatment of said breast or prostate cancer.

7. The method for treating a patient suffering from breast or prostate cancer in accordance with claim 6, wherein said isolated monoclonal antibody or antigen binding fragment thereof is humanized.

8. The method for treating a patient suffering from breast or prostate cancer in accordance with claim 6 comprising:
   conjugating said isolated monoclonal antibody or antigen binding fragment thereof with a member selected from the group consisting of toxins, radioactive compounds, and hermatogenous cells, whereby an antibody conjugate is formed; and
   administering said antibody conjugates is conjugated antigen binding fragments thereof to said patient;
   wherein said conjugated antibodies are placed in admixture with a pharmaceutically acceptable adjuvant and are administered in an amount effective to mediate treatment of said breast or prostate cancer.

9. The method of claim 8, wherein said isolated monoclonal antibody or antigen binding fragment thereof is humanized.

10. The method for treating a patient suffering from breast or prostate cancer in accordance with claim 6 wherein: said method of production is performed with a tissue sample containing cancerous and non-cancerous cells obtained from said patient.

\* \* \* \* \*